United States Patent
Kondo et al.

(10) Patent No.: US 7,892,711 B2
(45) Date of Patent: Feb. 22, 2011

(54) AZO COMPOUND, COMPOSITION FOR PHOTO-ALIGNMENT FILM USING THE SAME, AND METHOD FOR PRODUCING PHOTO-ALIGNMENT FILM

(75) Inventors: Hitoshi Kondo, Chiba (JP); Yasuhiro Kuwana, Chiba (JP); Hirokazu Takada, Sakura (JP); Vladimir Grigorievich Chigrinov, Hong Kong (CN); Hoi-Sing Kwok, Hong Kong (CN)

(73) Assignees: DIC Corporation, Tokyo (JP); Hong Kong University of Science & Technology, Hong Kong (CN)

( * ) Notice: Subject to any disclaimer, the term of this patent is extended or adjusted under 35 U.S.C. 154(b) by 1068 days.

(21) Appl. No.: 11/629,984

(22) PCT Filed: Jun. 28, 2005

(86) PCT No.: PCT/JP2005/011844
§ 371 (c)(1),
(2), (4) Date: Dec. 19, 2006

(87) PCT Pub. No.: WO2006/003893
PCT Pub. Date: Jan. 12, 2006

(65) Prior Publication Data
US 2007/0254220 A1 Nov. 1, 2007

(30) Foreign Application Priority Data
Jun. 30, 2004 (JP) ............................. P2004-194424
Sep. 3, 2004 (JP) ............................. P2004-257138

(51) Int. Cl.
G02F 1/1333 (2006.01)
C09K 19/00 (2006.01)
C09K 19/06 (2006.01)
C09K 19/52 (2006.01)

(52) U.S. Cl. ................. 430/20; 252/299.01; 252/299.6; 428/1.1; 428/1.3

(58) Field of Classification Search ............ 252/299.01, 252/299.1, 299.6; 428/1.1, 1.3; 430/20
See application file for complete search history.

(56) References Cited

U.S. PATENT DOCUMENTS 7,419,620 B2 * 9/2008 Buchecker et al. ..... 252/299.01
2002/0098295 A1 7/2002 Yip et al.

FOREIGN PATENT DOCUMENTS

| EP | 0525478 A2 | 2/1993 |
| JP | 2002-250924 | 9/2002 |
| JP | 2004-83810 | 3/2004 |
| JP | 2004-302272 | 10/2004 |
| JP | 2004-361653 | 12/2004 |
| JP | 2005-049386 A | 2/2005 |
| JP | 2005-173547 A | 6/2005 |
| JP | 2005-173548 A | 6/2005 |
| JP | 2005-173586 A | 6/2005 |

OTHER PUBLICATIONS

N. Novoseletski, et al.;"Alignment of Nematic Liquid Crystals by Photo-oriented layers;" Mol. Cryst. and Liq. Cryst.; vol. 352; 2000; pp. 27-35 (5 Sheets.).
S.I. Torgova, et al.; Influence of Chemical Structure on the Aligning Power of Photo-Oriented Films; Mol. Cryst. And Liq. Cryst.; vol. 360; 2001; pp. 81-91 (6 Sheets.).
V. Chigrinov, et al.; "Synthesis and properties of azo dye aligning layers for liquid crystal cells;" Liquid Crystals; vol. 29; No. 10; 2002; pp. 1321-1327.
Supplementary European Search Report dated Jul. 27, 2009 issued for EP Application No. 05765249.7.
A. X. Lupea et al. "Disazo-Pigments from Salicylamides" Chem. Bull. Univ. Timisoara, vol. 40, No. 54, 1995, pp. 57-62.
Notice of Reasons for Rejection mailed on Oct. 27, 2009, issued on the Japanese Patent Application No. 2006-528710 and the English translation thereof.

* cited by examiner

Primary Examiner—Geraldina Visconti
(74) Attorney, Agent, or Firm—Edwards Angell Palmer & Dodge LLP

(57) ABSTRACT

An azo compound of the present invention is represented by the general formula (1):

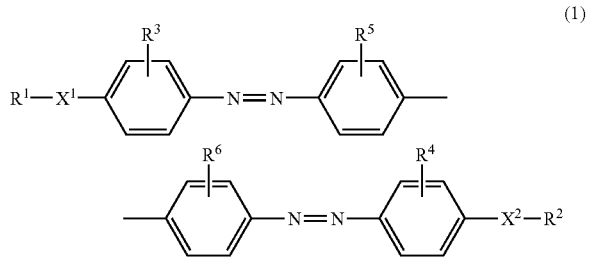

(wherein, $R^1$ and $R^2$ each independently represents a hydroxy group, or a polymerizable functional group selected from the group consisting of a (meth)acryloyl group, a (meth)acryloyloxy group, a (meth)acrylamide group, a vinyl group, a vinyloxy group, and a maleimide group; $X^1$ represents single bond when $R^1$ is a hydroxy group and represents a linking group represented by $-(A^1-B^1)_m-$ when $R^1$ is a polymerizable functional group; $X^2$ represents a single bond when $R^2$ is a hydroxy group and represents a linking group represented by $-(A^2-B^2)_n-$ when $R^2$ is a polymerizable functional group; $R^3$ and $R^4$ each independently represents $-OR^7$, a hydroxyalkyl group having 1 to 4 carbon atoms, or $-CONR^8R^9$; and $R^5$ and $R^6$ each independently represents a carboxy group, a sulfo group, a nitro group, amino group, or a hydroxy group).

10 Claims, 1 Drawing Sheet

AZO COMPOUND, COMPOSITION FOR PHOTO-ALIGNMENT FILM USING THE SAME, AND METHOD FOR PRODUCING PHOTO-ALIGNMENT FILM

TECHNICAL FIELD

The present invention relates to a novel azo compound, a composition for a liquid crystal alignment film using the same, and a method for producing the same and, more particularly, to a novel azo compound for a liquid crystal alignment film (hereinafter referred to as a photo-alignment film), which can align liquid crystal molecules by irradiating with light without rubbing, a composition for photo-alignment film, containing the same, and a method for producing a photo-alignment film by coating the composition for photo-alignment film.

BACKGROUND ART

In a liquid crystal display, a state of a molecular alignment of a liquid crystal is changed by an action of electric field so as to utilize a change in optical characteristics involved in the action for display. Mostly, the liquid crystal is used in the state of being sandwitched by two substrates. The inside of substrates is subjected to an aligning treatment so as to align liquid crystal molecules to a specific direction.

Usually, a rubbing method, which includes the steps of providing a polymer film made of polyimide on a substrate made of a glass and rubbing with a cloth in one direction, is used in the aligning treatment. Consequently, liquid crystal molecules, which are in contact with the substrate, are aligned so that the major axis (director) is parallel to the rubbing direction. Although the rubbing method has an advantage in that a production apparatus is simple, alignment defects are caused by scratch or dust on the surface of an alignment film in the production processes, and thus an adverse influence may be exerted on the resulting display characteristics. In a TFT type liquid crystal cell which has often been used, recently, a TFT element provided preliminarily on a substrate is broken by static electricity generated in the rubbing process, which results in decrease of the yield on production.

To the contrary, an intense interest has recently shown towards a technique for controlling a photo-alignment film without rubbing. Particularly, a photo-aligning method, which includes the step of irradiating a coating film provided on a substrate with polarized light to cause liquid crystal alignment, has intensively been studied because of simpleness. As the photo-aligning method, for example, a method by means of photoisomerization or rearrangement of a photo-aligning group capable of exerting a photo-aligning function in an organic molecule, for example, an azo group; a method by means of photodimerization of a cinnamoyl group, a cumarin group, or a chalcone group; a method by means of photocrosslinking of a benzophenone group; and a method by means of photolysis of a polyimide resin have been proposed.

Among these photo-aligning methods, a method utilizing azobenzene is attractive because high sensitivity and high alignment-regulating force is obtained. For example, a method, which includes the step of irradiating an azo compound represented by the formula (A) with light having anisotropy thereby producing a photo-alignment film, is known (for example, see non-patent reference 1). Also, there is known an azo compound represented by the formula (B) in which a polymerizable functional group is included in an azo compound for the purpose of stabilizing an alignment state of these photo-aligning groups (for example, see patent reference 1).

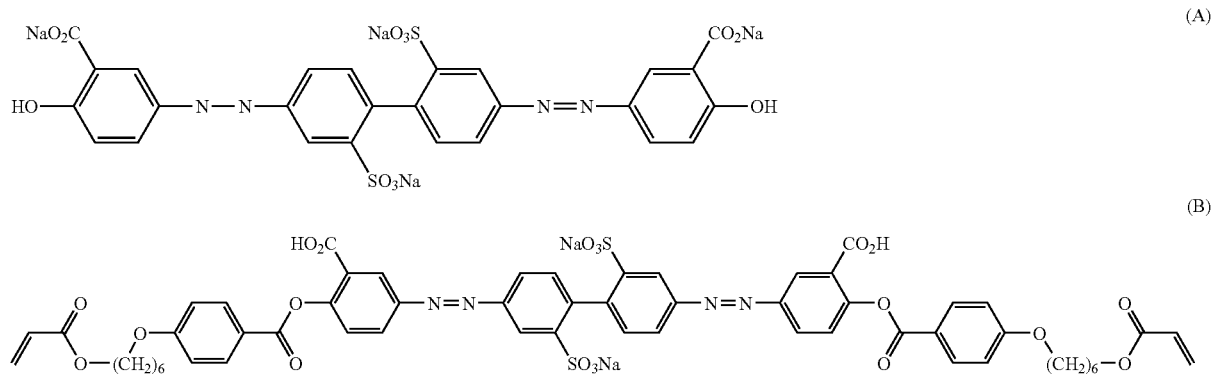

The patent reference 1 discloses a method including the steps of coating a composition for photo-alignment film containing a dichromatic dye having one or more polymerizable functional groups in a molecule on a substrate, irradiating the coated substrate with polarized light thereby imparting a liquid crystal aligning function, and polymerizing the polymerizable functional groups through heating or light irradiation to obtain a photo-alignment film. The dichromatic dye is low molecular and can be simply aligned, and also it has two or more polymerizable functional group and can be easily polymerized, and thus a photo-alignment film having excellent long-term stability can be provided.

However, the liquid crystal device using the photoalignment film obtained by the method had a problem such as a low voltage-holding ratio. It is necessary to hold the applied voltage until the following writing in a TFT type liquid crystal cell, and a problem such as flickering of a screen arises when the voltage-holding ratio is low. Therefore, it is an important object to improve the voltage-holding ratio so as to put a photo-alignment film into practical use.

[Non-patent reference 1] Molecular Crystals and Liquid Crystals, 2000 (352), p 27, the same document 2001 (360), p 81, and Liquid Crystals, 2002 (29), p 1321).

[Patent reference 1] Japanese Unexamined Patent Application, First Publication No. 2002-250924.

DISCLOSURE OF THE INVENTION

An object to be achieved by the present invention is to provide a novel azo compound used to produce a photo-alignment film which exhibits good alignment properties and also exhibits a high voltage-holding ratio even at high temperature, and a composition for photo-alignment film using the same, and a method for producing the photo-alignment film.

The present inventors considered that carboxy groups of azo compounds represented by the compounds (A) and (B) exert an adverse influence on the voltage-holding ratio, and they have intensively studied and found that a liquid crystal device capable of achieving a high voltage-holding ratio even at high temperature can be obtained by using, as an alignment film, an azo compound in which a carboxy group is substituted by an alkoxy group, an acid amide group, or a hydroxyalkyl group. Thus, the object has been achieved.

Namely, the present invention provides an azo compound represented by a general formula (1):

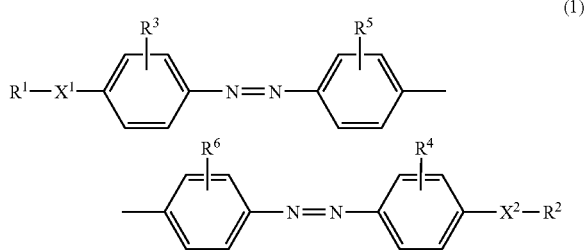

(wherein, $R^1$ and $R^2$ each independently represents a hydroxy group, or a polymerizable functional group selected from the group consisting of a (meth)acryloyl group, a (meth)acryloyloxy group, a (meth)acrylamide group, a vinyl group, a vinyloxy group, and a maleimide group; $X^1$ represents single bond when $R^1$ is a hydroxy group and represents a linking group represented by $-(A^1-B^1)_m-$ when $R^1$ is a polymerizable functional group; $X^2$ represents a single bond when $R^2$ is a hydroxy group and represents a linking group represented by $-(A^2-B^2)_n-$ when $R^2$ is a polymerizable functional group, wherein $A^1$ is bonded to $R^1$, $A^2$ is bonded to $R^2$, and $B^1$ and $B^2$ each is bonded to an adjacent phenylene group; $A^1$ and $A^2$ each independently represents a single bond, or a phenylene or arylene group which may have a linear alkylene group having 1 to 18 carbon atoms, a branched alkylene group having 1 to 18 carbon atoms, or a linear or branched alkoxy group having 1 to 18 carbon atoms; $B^1$ and $B^2$ each independently represents a single bond, —O—, —CO—O—, —O—CO—, —CO—NH—, —NH—CO—, —NH—CO—O—, or —O—CO—NH—; m and n each independently represents an integer of 0 to 4, provided that a plurality of $A^1$(s), $B^1$(s), $A^2$(s) and $B^2$(s) is the same or different when m or n is 2 or more, $A^1$ or $A^2$ interposed between two $B^1$(s) or $B^2$(s) is not a single bond, and a combination of $A^1$ and $B^1$ or a combination of $A^2$ and $B^2$ is not a combination of only a linear alkylene group and —O—; $R^3$ and $R^4$ each independently represents —$OR^7$ (wherein, $R^7$ represents an alkyl group having 2 to 6 carbon atoms, a cycloalkyl group having 3 to 6 carbon atoms, or an alkyl group having 1 to 6 carbon atoms substituted with a lower alkoxy group having 1 to 6 carbon atoms), a hydroxyalkyl group having 1 to 4 carbon atoms, or —$CONR^8R^9$ (wherein, $R^8$ and $R^9$ each independently represents a hydrogen atom or an alkyl group having 1 to 6 carbon atoms); and $R^5$ and $R^6$ each independently represents a carboxy group, a sulfo group, a nitro group, amino group, or a hydroxy group, provided that a carboxy group and a sulfo group may be bonded to an alkali metal to form a salt).

Also, the present invention provides a composition for photo-alignment film, which contains an azo compound represented by the general formula (1), and a method for producing a photo-alignment film, which includes coating the composition for photo-alignment film on a substrate, and irradiating the coated substrate with light having anisotropy.

In the present invention, "(meth)acryl" means either or both of acryl and methacryl. Also "(meth)acryloyl" means either or both of acryloyl and methacryloyl.

The azo compound represented by the general formula (1) is easily aligned in a fixed direction to a polarization plane or an incidence plane by irradiation with light having anisotropy such as polarized light or incident light from a tilted direction to a film plane, and thus a film having high anisotropy in the plane and a high alignment-regulating force is obtained. The resulting alignment film exhibits a high voltage-holding ratio.

Since the azo compound represented by the general formula (1) has a carboxy group, a sulfo group, a nitro group, an amino group, or a hydroxy group as $R^5$ and $R^6$, the photo-alignment film composition of the present invention exhibits high affinity with a glass substrate or an oxide transparent electrode such as ITO. Therefore, a uniform coating film can be obtained by coating a solution of the photo-alignment film composition of the present invention on a substrate and removing a solvent with drying, and a photo-alignment film having both good alignment-regulating force and voltage-holding ratio can be obtained by a photo-alignment operation. Furthermore, a photo-alignment film having high stability can be obtained by polymerizing polymerizable functional groups through heating or light irradiation.

BEST MODE FOR CARRYING OUT THE INVENTION

Figure 1:
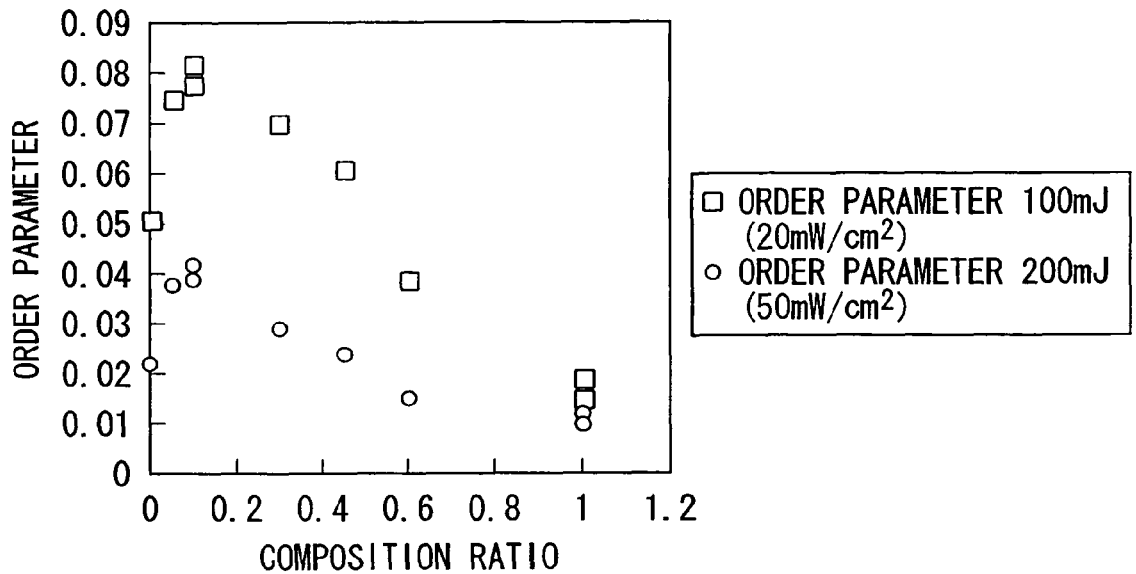
FIG. 1 is a graph showing a relation between a value of a ratio of the content of a compound represented by the general formula (1-1) to the sum of the content of a compound represented by the general formula (1-1) and the content of a compound represented by the general formula (2), as a "composition ratio", and an order parameter.

Azo Compound Represented By the General Formula (1)

In the general formula (1), $R^1$ and $R^2$ each independently represents a hydroxy group, or a polymerizable functional group selected from the group consisting of a (meth)acryloyl group, a (meth)acryloyloxy group, a (meth)acrylamide group, a vinyl group, a vinyloxy group, and a maleimide group. $R^1$ and $R^2$ preferably represent a polymerizable functional group in view of stability to light or heat. Among polymerizable functional groups, a (meth)acryloyloxy group or a maleimide group is particularly preferable.

$X^1$ represents single bond when $R^1$ is a hydroxy group and represents a linking group represented by -$(A^1$-$B^1)_m$- when $R^1$ is a polymerizable functional group; and $X^2$ represents a single bond when $R^2$ is a hydroxy group and represents a linking group represented by -$(A^2$-$B^2)_n$- when $R^2$ is a polymerizable functional group. $A^1$ and $A^2$ each independently represents a single bond, or a divalent hydrocarbon group. Examples of the divalent hydrocarbon group represented by $A^1$ and $A^2$ include linear alkylene groups having 1 to 18 carbon atoms, such as a methylene group, an ethylene group, a trimethylene group, a tetramethylene group, a pentamethylene group, a hexamethylene group, a heptamethylene group, an octamethylene group, a nonamethylene group, a decamethylene group, an undecamethylene group, and a dodecamethylene group; branched alkylene groups having 1 to 18 carbon atoms, such as a 1-methylethylene group, a 1-ethyltriethylene group, a 2-methyltriethylene group, a 1-methyltetraethylene group, a 2-methyltetraethylene group, a 1-methylpentamethylene group, a 2-methylpentamethylene group, and a 3-methylpentamethylene group; phenylene groups such as a p-phenylene group; phenylene groups having a linear or branched alkoxy group having 1 to 18 carbon atoms, such as a 2-methoxy-1,4-phenylene group, a 3-methoxy-1,4-phenylene group, a 2-ethoxy-1,4-phenylene group, a 3-ethoxy-1,4-phenylene group, and a 2,3,5-trimethoxy-1,4-phenylene group; and arylene groups such as a 2,6-naphthalenediyl group. Herein, a linking group is excluded, in which a combination of $A^1$ and $B^1$ or a combination of $A^2$ and $B^2$ is a combination of only a linear alkylene group and —O—.

$B^1$ and $B^2$ each independently represents a single bond, —O—, —CO—O—, —O—CO—, —CO—NH—, —NH—CO—, —NH—CO—O—, or —O—CO—NH—. m and n each independently represents an integer of 0 to 4 provided that a plurality of $A^1$(s), $B^1$(s), $A^2$(s) and $B^2$(s) may be the same or different when m or n is 2 or more, and $A^1$ or $A^2$ interposed between two $B^1$(s) or $B^2$(s) is not a single bond. $X^1$ and $X^2$ in the general formula (1) may be the same or different.

When $R^1$ or $R^2$ is a (meth)acryloyloxy group, it is more preferable that linking groups $X^1$ and $X^2$ have the structure represented by the following formula (3) (the structure of -$(A^1$-$B^1)_m$- in which m is 2, namely, the structure of $A^1$-$B^1$-$A^1$-$B^1$-, $A^1$: —$(CH_2)_p$-, $B^1$: —O—, $A^1$: phenylene group, $B^1$: —COO—) because a high alignment-regulating force can be obtained when used as the composition for photo-alignment film:

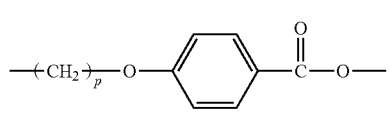

(3)

(wherein, p represents an integer of 1 to 18).

In the general formula (1), $R^3$ and $R^4$ each independently represents —$OR^7$ (wherein, $R^7$ represents an alkyl group having 2 to 6 carbon atoms, a cycloalkyl group having 3 to 6 carbon atoms, or an alkyl group having 1 to 6 carbon atoms substituted with a lower alkoxy group having 1 to 6 carbon atoms), a hydroxyalkyl group having 1 to 4 carbon atoms (the hydroxyalkyl group represents an alkyl group substituted with a hydroxy group), or —$CONR^8R^9$ (wherein $R^8$ and $R^9$ each independently represents a hydrogen atom or an alkyl group having 1 to 6 carbon atoms).

Specific examples of the alkyl group having 2 to 6 carbon atoms represented by $R^7$ include an ethyl group, propyl group, a butyl group, a pentyl group, a hexyl group, and a 1-methylethyl group. Among these alkyl groups, an ethyl group and a propyl group are particularly preferable.

Examples of the cycloalkyl group having 3 to 6 carbon atoms represented by $R^7$ include a cyclopropyl group, a cyclobutyl group, a cyclopentyl group, and a cyclohexyl group.

Examples of the alkyl group having 1 to 6 carbon atoms substituted with a lower alkoxy group having 1 to 6 carbon atoms represented by $R^7$ include a methoxymethyl group and a 1-ethoxyethyl group. Like a tetrahydropyranyl group, a cyclic structure may be formed. Among these groups, a methoxymethyl group is particularly preferable.

Specific examples of the hydroxyalkyl group having 1 to 4 carbon atoms represented by $R^7$ include a hydroxymethyl group, a 1-hydroxyethyl group, a 2-hydroxyethyl group, a 1-hydroxypropyl group, a 2-hydroxypropyl group, a 3-hydroxypropyl group, and a 1-hydroxybutyl group. Among these hydroxyalkyl groups, a hydroxymethyl group is particularly preferable.

Examples of the alkyl group having 1 to 6 carbon atoms represented by $R^8$ and $R^9$ include a methyl group, an ethyl group, a propyl group, a butyl group, a pentyl group, a hexyl group, and a 1-methylethyl group.

A hydrogen atom, a methyl group, an ethyl group, a propyl group, a butyl group, and a pentyl group are particularly preferable as $R^8$ and $R^9$.

It is particularly preferable that $R^3$ and $R^4$ are substituted on the meta-position of phenylene groups at both ends of a 4,4'-(bisphenylazo)biphenyl backbone because excellent photo-alignment properties are obtained.

In the general formula (1), $R^5$ and $R^6$ each independently represents a carboxy group, a sulfo group, a nitro group, an amino group, or a hydroxy group provided that a carboxy group or a sulfo group may be bonded to an alkali metal to form a salt.

In order to uniformly form an alignment film on the surface of the substrate, a functional group having high affinity with a transparent electrode made of glass or ITO is preferable, and a carboxy group and a sulfo group are more preferable, and a sulfo group or a salt thereof are particularly preferable.

A compound represented by the general formula (1') in which $R^5$ and $R^6$ are substituted on the 2- and 2'-positions of the 4,4'-bis(phenylazo)biphenyl backbone is particularly preferable because excellent photo-alignment properties are obtained:

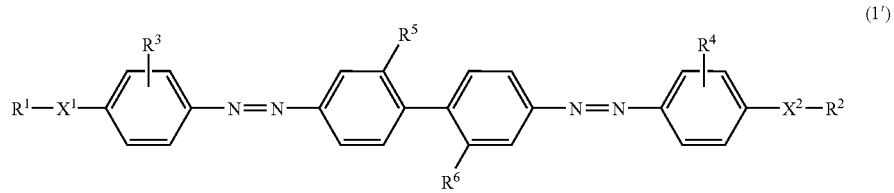

(1')

(wherein, $R^1$ to $R^6$, and $X^1$ and $X^2$ represent the same group as those represented by the general formula (1)).

Among the compounds represented by the general formulas (1) and (1'), a compound in which $R^3$ and/or $R^4$ represent —$OR^7$ or the hydroxyalkyl group is particularly preferable because excellent photo-alignment properties are obtained.

When using a compound (1-1) in which at least one of $R^3$ and $R^4$ is —$CONR^8R^9$ among the compounds represented by the general formula (1) in combination with an azo compound represented by the general formula (2) described hereinafter, a photo-alignment film, which has high sensitivity and attains sufficient liquid crystal alignment properties in a low dose, can be obtained. A compound (1-1') in which the general formula (1) is (1') and at least one of $R^3$ and $R^4$ is —$CONR^8R^9$ is particularly preferable:

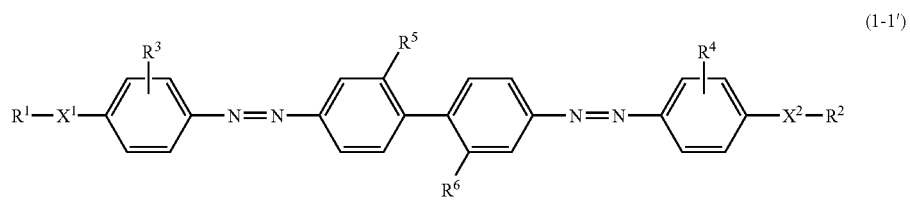

(1-1')

(wherein, $R^1$ to $R^6$, $X^1$ and $X^2$ represent the same groups as those represented by the general formula (1), provided that at least one of $R^3$ and $R^4$ represents —$CONR^8R^9$ (wherein, $R^8$ and $R^9$ each independently represents a hydrogen atom or an alkyl group having 1 to 6 carbon atoms)).

(Production Method)

The azo compound represented by the general formula (1) can be easily synthesized, for example, by the following method. Namely, a diazonium salt is synthesized by the diazotization reaction between a benzidine derivative and sodium nitrite. Then, the diazonium salt mixture obtained in the above process is reacted with a phenol derivative to obtain an azo compound having a hydroxy group.

The azo compound thus obtained is reacted with carboxylic acid, carboxylic acid chloride, carboxylic anhydride, or an alkyl halide, each having a polymerizable functional group such as acryloyloxy group or maleimide group in the following scheme to obtain an azo compound having a polymerizable functional group.

Examples of a specific aspect of the azo compound represented by the general formula (1) according to the present invention will now be descried, but the method for producing the azo compound of the present invention is not limited to these production methods:

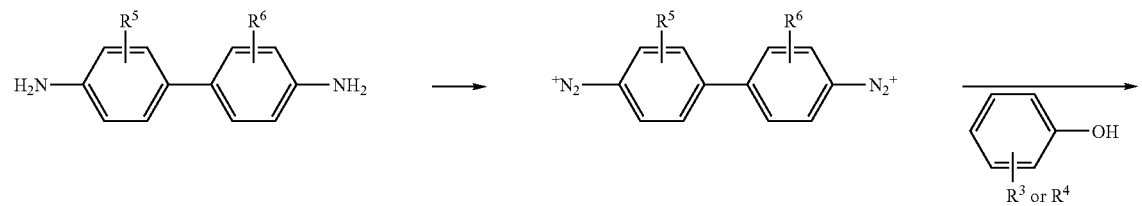

-continued
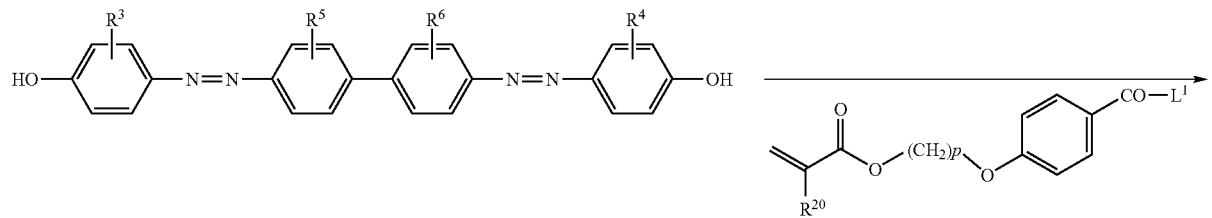
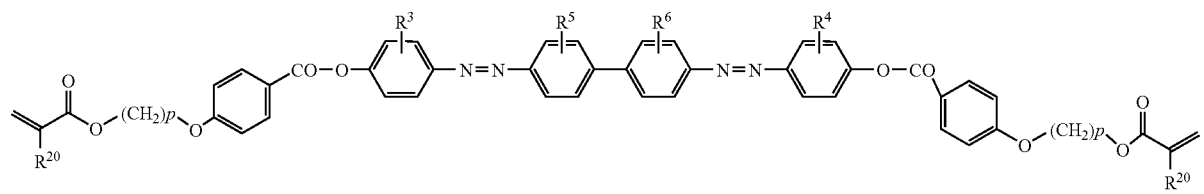
(wherein, $R^3$ to $R^6$ are as defined in the general formula (1), $R^{20}$ represents hydrogen or a methyl group, p represents an integer of 1 to 18, and $L^1$ represents a hydroxyl group, a chlorine atom, or a pivaloyl group);
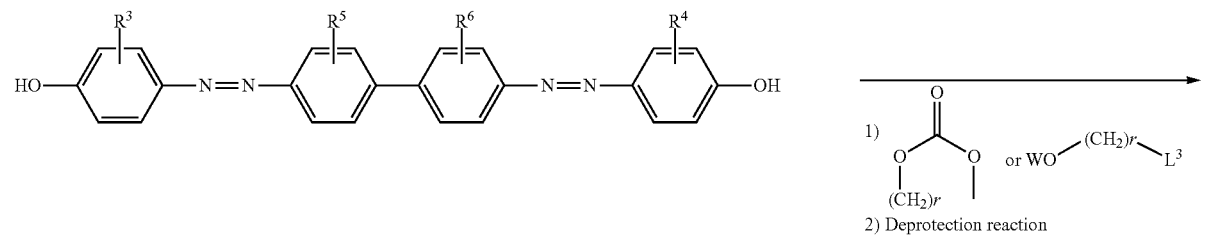
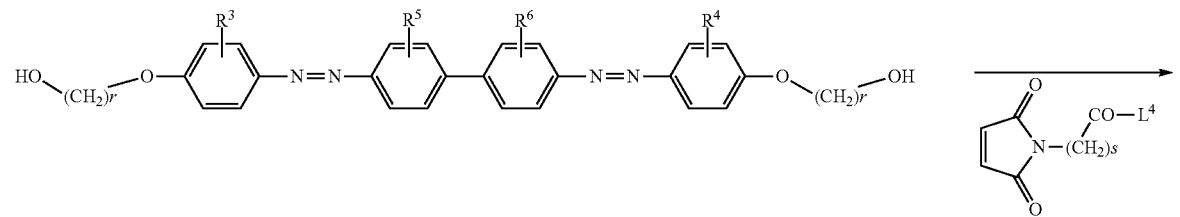
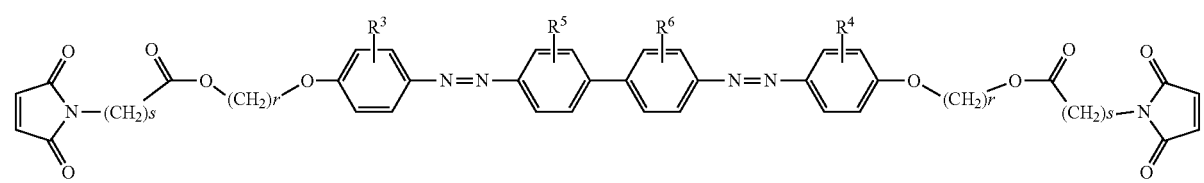

(wherein, $R^3$ to $R^6$ are as defined in the general formula (1), r represents an integer of 1 to 18, s represents an integer of 1 to 4, w represents a hydrogen atom, or a protective group such as an acetyl group, a benzoyl group, a tetrahydropyranyl group, a methoxymethyl group, or a t-butyldimethylsilyl group, $L^3$ represents a chlorine atom, a bromine atom, an iodine atom, or a sulfonate ester group such as a methanesulfonyloxy group, and $L^4$ represents a hydroxyl group, a chlorine atom, or a pivaloyloxy group);

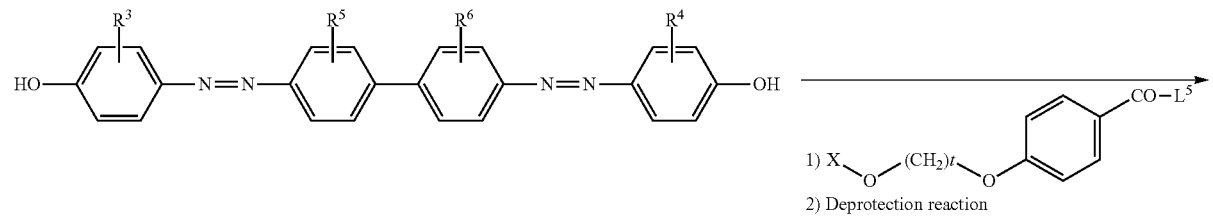

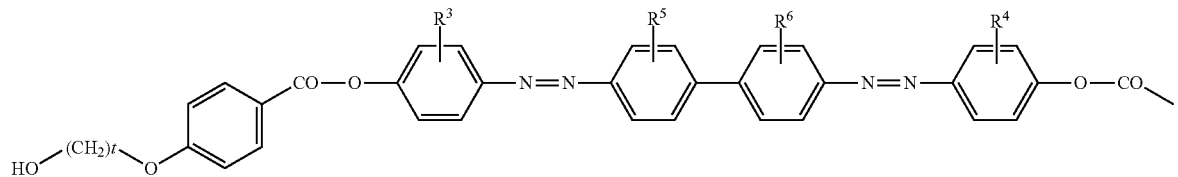

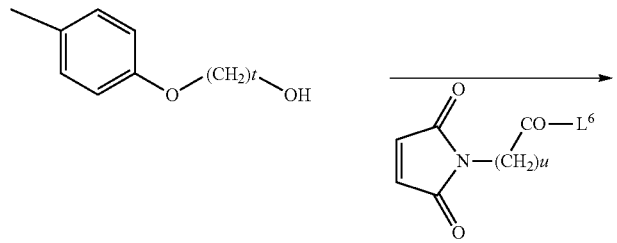

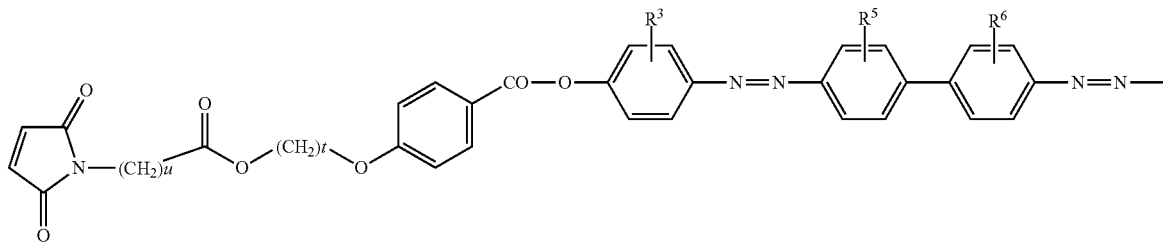

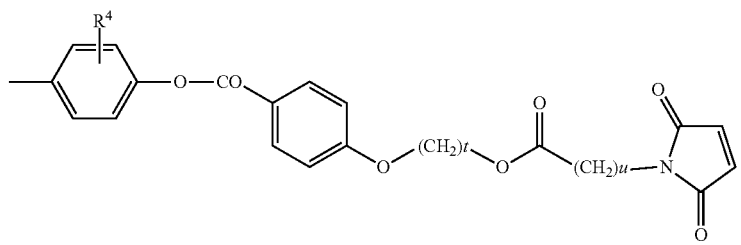

(wherein, $R^3$ to $R^6$ are as defined in the general formula (1), t represents an integer of 1 to 18, u represents an integer of 1 to 4, X represents a hydrogen atom, or a protective group such as acetyl group, benzoyl group, tetrahydropyranyl group, methoxymethyl group, or t-butyldimethylsilyl group, and $L^5$ and $L^6$ each independently represents a hydroxyl group, a chlorine atom, or a pivaloyloxy group).

SPECIFIC EXAMPLES

Specific structures of the azo compound represented by the general formula (1) of the present invention produced by the above method are shown in Tables 1 to 4. $R^1$ to $R^6$, and $X^1$ and $X^2$ in the table are as defined in the general formula (1). The substitution position of $R^3$ to $R^6$ is indicated by the position number represented by the general formula (1b). The formulas (3a) to (3f) and (4) in Tables 1 to 4 mean the following structures.

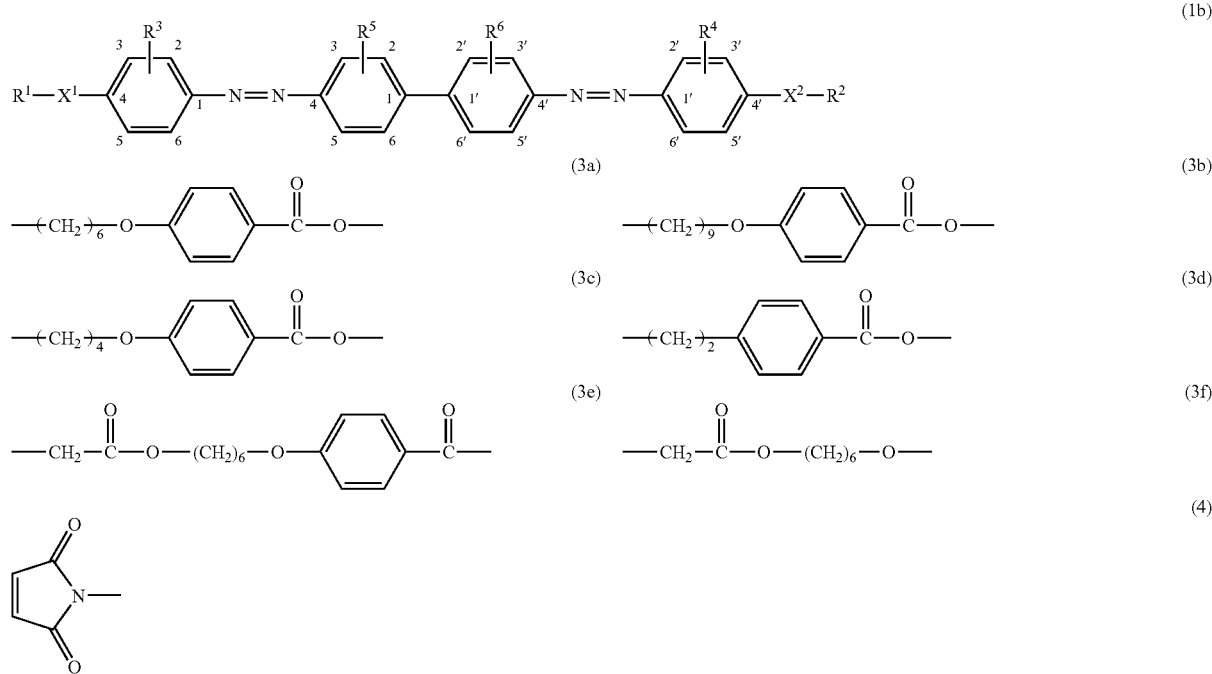

TABLE 1

| Compound No. | $R^1$ | $X^1$ | $R^2$ | $X^2$ | $R^3$ | $R^4$ | $R^5$ | $R^6$ |
|---|---|---|---|---|---|---|---|---|
| A-1 | OH | Single bond | OH | Single bond | 3-OCH$_2$CH$_3$ | 3'-OCH$_2$CH$_3$ | 2-SO$_3$Na | 2'-SO$_3$Na |
| A-2 | OH | Single bond | OH | Single bond | 3-OCH$_2$CH$_3$ | 3'-OCH$_2$CH$_3$ | 2-SO$_3$H | 2'-SO$_3$H |
| A-3 | OH | Single bond | OH | Single bond | 3-OCH$_2$CH$_2$-CH$_3$ | 3'-OCH$_2$CH$_2$-CH$_3$ | 2-SO$_3$Na | 2'-SO$_3$Na |
| A-4 | OH | Single bond | OH | Single bond | 3-OCH$_2$CH$_2$-CH$_3$ | 3'-OCH$_2$CH$_2$-CH$_3$ | 2-SO$_3$H | 2'-SO$_3$H |
| A-5 | OH | Single bond | OH | Single bond | 3-OCH-(CH$_3$)$_2$ | 3'-OCH(CH$_3$)$_2$ | 2-SO$_3$Na | 2'-SO$_3$Na |
| A-6 | OH | Single bond | OH | Single bond | 3-OCH-(CH$_3$)$_2$ | 3'-OCH(CH$_3$)$_2$ | 2-SO$_3$H | 2'-SO$_3$H |
| A-7 | OH | Single bond | OH | Single bond | 3-OCH$_2$O-CH$_3$ | 3'-OCH$_2$OCH$_3$ | 2-SO$_3$Na | 2'-SO$_3$Na |
| A-8 | CH$_2$CH-COO | Formula (3a) | CH$_2$CH-COO | Formula (3a) | 3-OCH$_2$CH$_3$ | 3'-OCH$_2$CH$_3$ | 2-SO$_3$Na | 2'-SO$_3$Na |
| A-9 | CH$_2$CH-COO | Formula (3b) | CH$_2$CH-COO | Formula (3b) | 3-OCH$_2$CH$_3$ | 3'-OCH$_2$CH$_3$ | 2-SO$_3$Na | 2'-SO$_3$Na |
| A-10 | CH$_2$CH-COO | Formula (3a) | CH$_2$CH-COO | Formula (3a) | 3-OCH$_2$O-CH$_3$ | 3'-OCH$_2$OCH$_3$ | 2-SO$_3$Na | 2'-SO$_3$Na |

TABLE 2

| Compound No. | $R^1$ | $X^1$ | $R^2$ | $X^2$ | $R^3$ | $R^4$ | $R^5$ | $R^6$ |
|---|---|---|---|---|---|---|---|---|
| B-1 | OH | Single bond | OH | Single bond | 3-CH$_2$OH | 3'-CH$_2$OH | 2-SO$_3$Na | 2'-SO$_3$Na |
| B-2 | OH | Single bond | OH | Single bond | 3-CH$_2$OH | 3'-CH$_2$OH | 2-SO$_3$H | 2'-SO$_3$H |
| B-3 | OH | Single bond | OH | Single bond | 3-CH(OH)CH$_3$ | 3'-CH(OH)CH$_3$ | 2-SO$_3$Na | 2'-SO$_3$Na |
| B-4 | OH | Single bond | OH | Single bond | 3-CH(OH)CH$_3$ | 3'-CH(OH)CH$_3$ | 2-SO$_3$H | 2'-SO$_3$H |
| B-5 | OH | Single bond | OH | Single bond | 3-CH$_2$CH$_2$OH | 3'-CH$_2$CH$_2$OH | 2-SO$_3$Na | 2'-SO$_3$Na |
| B-6 | OH | Single bond | OH | Single bond | 3-CH$_2$CH$_2$OH | 3'-CH$_2$CH$_2$OH | 2-SO$_3$H | 2'-SO$_3$H |
| B-7 | CH$_2$CHCOO | Formula (3c) | CH$_2$CHCOO | Formula (3c) | 3-CH$_2$OH | 3'-CH$_2$OH | 2-SO$_3$Na | 2'-SO$_3$Na |
| B-8 | CH$_2$CHCOO | Formula (3a) | CH$_2$CHCOO | Formula (3a) | 3-CH$_2$OH | 3'-CH$_2$OH | 2-SO$_3$Na | 2'-SO$_3$Na |

TABLE 2-continued

| Compound No. | $R^1$ | $X^1$ | $R^2$ | $X^2$ | $R^3$ | $R^4$ | $R^5$ | $R^6$ |
|---|---|---|---|---|---|---|---|---|
| B-9 | $CH_2CHCOO$ | Formula (3b) | $CH_2CHCOO$ | Formula (3b) | 3-$CH_2OH$ | 3'-$CH_2OH$ | 2-$SO_3Na$ | 2'-$SO_3Na$ |
| B-10 | $CH_2CHCOO$ | Formula (3d) | $CH_2CHCOO$ | Formula (3d) | 3-$CH_2OH$ | 3'-$CH_2OH$ | 2-$SO_3Na$ | 2'-$SO_3Na$ |
| B-11 | $CH_2C(CH_3)COO$ | Formula (3a) | $CH_2C(CH_3)COO$ | Formula (3a) | 3-$CH_2OH$ | 3'-$CH_2OH$ | 2-$SO_3Na$ | 2'-$SO_3Na$ |

TABLE 3

| Compound No. | $R^1$ | $X^1$ | $R^2$ | $X^2$ | $R^3$ | $R^4$ | $R^5$ | $R^6$ |
|---|---|---|---|---|---|---|---|---|
| C-1 | OH | Single bond | OH | Single bond | 3-$CONH_2$ | 3'-$CONH_2$ | 2-$SO_3Na$ | 2'-$SO_3Na$ |
| C-2 | OH | Single bond | OH | Single bond | 3-$CONH_2$ | 3'-$CONH_2$ | 2-$SO_3H$ | 2'-$SO_3H$ |
| C-3 | OH | Single bond | OH | Single bond | 3-$CONH$-$(CH_3)$ | 3'-$CONH(CH_3)$ | 2-$SO_3Na$ | 2'-$SO_3Na$ |
| C-4 | OH | Single bond | OH | Single bond | 3-$CONH$-$(CH_3)$ | 3'-$CONH(CH_3)$ | 2-$SO_3H$ | 2'-$SO_3H$ |
| C-5 | OH | Single bond | OH | Single bond | 3-$CON$-$(CH_3)_2$ | 3'-$CON(CH_3)_2$ | 2-$SO_3Na$ | 2'-$SO_3Na$ |
| C-6 | OH | Single bond | OH | Single bond | 3-$CON(CH_3)_2$ | 3'-$CON(CH_3)_2$ | 2-$SO_3H$ | 2'-$SO_3H$ |
| C-7 | OH | Single bond | OH | Single bond | 3-$CONH$-$(n$-$C_4H_9)$ | 3'-$CONH(n$-$C_4H_9)$ | 2-$SO_3Na$ | 2'-$SO_3Na$ |
| C-8 | OH | Single bond | OH | Single bond | 3-$CONH$-$(n$-$C_4H_9)$ | 3'-$CONH(n$-$C_4H_9)$ | 2-$SO_3H$ | 2'-$SO_3H$ |
| C-9 | $CH_2CH$-$COO$ | Formula (3a) | $CH_2CH$-$COO$ | Formula (3a) | 3-$CONH_2$ | 3'-$CONH_2$ | 2-$SO_3Na$ | 2'-$SO_3Na$ |
| C-10 | $CH_2CH$-$COO$ | Formula (3a) | $CH_2CH$-$COO$ | Formula (3a) | 3-$CONH$-$(n$-$C_4H_9)$ | 3'-$CONH(n$-$C_4H_9)$ | 2-$SO_3Na$ | 2'-$SO_3Na$ |

TABLE 4

| Compound No. | $R^1$ | $X^1$ | $R^2$ | $X^2$ | $R^3$ | $R^4$ | $R^5$ | $R^6$ |
|---|---|---|---|---|---|---|---|---|
| D-1 | OH | Single bond | OH | Single bond | 3-$OCH_2CH_3$ | 3'-$OCH_2CH_3$ | 2-$CO_2H$ | 2'-$CO_2H$ |
| D-2 | OH | Single bond | OH | Single bond | 3-$CH_2OH$ | 3'-$CH_2OH$ | 2-$CO_2H$ | 2'-$CO_2H$ |
| D-3 | OH | Single bond | OH | Single bond | 3-$CONH_2$ | 3'-$CONH_2$ | 2-$CO_2H$ | 2'-$CO_2H$ |
| D-4 | OH | Single bond | OH | Single bond | 3-$CONH$-$(n$-$C_4H_9)$ | 3-$CONH$-$(n$-$C_4H_9)$ | 2-$CO_2H$ | 2'-$CO_2H$ |
| D-5 | $CH_2CH$-$COO$ | Formula (3a) | $CH_2CH$-$COO$ | Formula (3a) | 3-$OCH_2CH_3$ | 3'-$OCH_2CH_3$ | 2-$CO_2h$ | 2'-$CO_2H$ |
| D-6 | $CH_2CH$-$COO$ | Formula (3a) | $CH_2CH$-$COO$ | Formula (3a) | 3-$CH_2OH$ | 3'-$CH_2OH$ | 2-$CO_2H$ | 2'-$CO_2H$ |
| D-7 | $CH_2CH$-$COO$ | Formula (3a) | $CH_2CH$-$COO$ | Formula (3a) | 3-$CONH$-$(n$-$C_4H_9)$ | 3'-$CONH$-$(n$-$C_4H_9)$ | 2-$CO_2H$ | 2'-$CO_2H$ |
| D-8 | Formula (4) | Formula (3e) | Formula (4) | Formula (3e) | 3-$OCH_2CH_3$ | 3'-$OCH_2CH_3$ | 2-$SO_3Na$ | 2'-$SO_3Na$ |
| D-9 | Formula (4) | Formula (3f) | Formula (4) | Formula (3f) | 3-$OCH_2CH_3$ | 3'-$OCH_2CH_3$ | 2-$SO_3Na$ | 2'-$SO_3Na$ |
| D-10 | Formula (4) | Formula (3e) | Formula (4) | Formula (3e) | 3-$CH_2OH$ | 3'-$CH_2OH$ | 2-$SO_3Na$ | 2'-$SO_3Na$ |
| D-11 | Formula (4) | Formula (3e) | Formula (4) | Formula (3e) | 3-$CON(CH_3)_2$ | 3'-$CON(CH_3)_2$ | 2-$SO_3Na$ | 2'-$SO_3Na$ |

(Composition for Photo-alignment Film)

The composition for photo-alignment film of the present invention is not specifically limited as long as it contains the azo compound represented by the general formula (1) and may include only the azo compound represented by the general formula (1). Also, it is possible to add other components, for example, additives such as solvents for improving coatability to the substrate, polymerization initiators, polymer materials for adjusting viscosity of the composition, leveling agents, thixotropic agents, gelatinizers, thickeners, surfactants, ultraviolet absorbers, infrared absorbers, antioxidants, and surface treating agents as long as alignment capability of the liquid crystal does not drastically deteriorate.

The solvent, which can be used in the composition for photo-alignment film of the present invention, is not specifically limited as long as it can dissolve the azo compound represented by the general formula (1), and examples thereof include N-methyl pyrrolidone, 2-butoxyethanol, N,N-dimethylformamide,γ-butyrolactone, dimethyl sulfoxide, ethylene glycol, toluene, tetrahydrofuran, chlorobenzene, dimethylformamide, γ-butyrolactone, dimethyl sulfoxide, ethylene glycol, toluene, tetrahydrofuran, chlorobenzene, and N,N-dimethyl acetamide. Among these solvents, a solution of N-methyl pyrrolidone, butylcellosolve, or N,N-dimethylformamide is preferable because the solution is excellent in coatability to the substrate made of glass and a uniform film can be obtained. These solvents are preferably selected taking account of coatability and a volatilization rate of the solvent after coating, and two or more kinds thereof can be used in combination.

Since the solvent is removed by volatilization after coating on the substrate, it is necessary that the concentration of the azo compound represented by the general formula (1) is adjusted to at least 0.2% by mass, and particularly preferably within a range from 0.5 to 10% by mass.

The polymer material for adjusting viscosity of the composition for photo-alignment film of the present invention includes, for example, a material which can form a film on the substrate and has high solubility to the solvent, and is also excellent in compatibility with the azo compound represented by the general formula (1). Specific examples thereof include polyvinyl alcohol, polyimide, polymaleimide, polyester, and polyamide. Among these polymer materials, polyimide is particularly preferable because it is excellent in heat resistance and film forming properties on the substrate. In order to prevent deterioration of photo-alignment properties caused by the azo compound represented by the general formula (1), the content of these polymer materials is preferably 60% or less, and particularly preferably 30% or less, based on the solid content of the photo-alignment film composition.

When the azo compound represented by the general formula (1) has a polymerizable functional group as $R^1$ or $R^2$, a small amount of a thermal polymerization initiator or a photopolymerization initiator is preferably added for the purpose of increasing a polymerization rate. As these polymerization initiators, known polymerization initiators can be used. Since liquid crystal display characteristics may deteriorate when the amount is too large, the content of the polymerization initiator is preferably adjusted to 5% or less based on the solid content.

It is preferred to use an azo compound (1-1) in which at least one of $R^3$ and $R^4$ is —$CONR^8R^9$ (wherein $R^8$ and $R^9$ each independently represents a hydrogen atom or an alkyl group having 1 to 6 carbon atoms) among the azo compound represented by the general formula (1) in combination with an azo compound represented by the general formula (2) because a photo-alignment film, which has high sensitivity and attains sufficient liquid crystal alignment properties in a low dose, can be obtained. Specifically, a photo-alignment film, which has particularly high sensitivity to ultraviolet light and visible light and also has sufficient liquid crystal alignment capability in a low dose, can be obtained. For example, when irradiated with parallel light of unpolarized ultraviolet light from an angle of 45° diagonally, a photo-alignment film having an absolute value of an order parameter of 0.02 or more can be obtained at a light intensity of 250 mJ or less:

(wherein, $R^7$ to $R^{12}$, and $X^3$ and $X^4$ represent the same groups as those represented by the general formula (2)).

Also, a composition for photo-alignment film containing a compound represented by the general formula (1-1') and a compound represented by the general formula (2') can be exemplified as a preferable aspect.

A mixing ratio of the azo compound (1-1) to a compound represented by the general formula (2) is preferably a mixing ratio so that a ratio of the content of the azo compound (1-1) is from 0.02 to 0.5 based on the sum of the content of the azo compound (1-1) and the content of the compound represented by the general formula (2). When the mixing ratio is from 0.05 to 0.3, sufficient liquid crystal alignment capability can be obtained in a low dose.

The reason why the composition has high sensitivity can be considered as follows. Namely, a complex is formed by the interaction between an amide group of the azo compound (1-1) and a carboxy group of the compound represented by the general formula (2), and sensitivity to light increases as compared with the case where only the compound represented by the general formula (2) is used, and thus it becomes easy to realign an azo group.

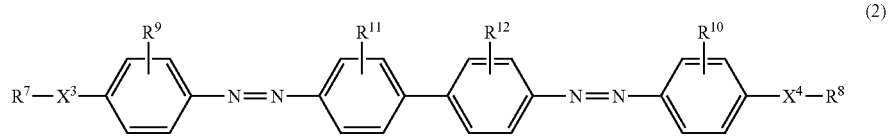

(2)

(wherein, $R^7$ and $R^8$ represent the same groups as those represented by $R^1$ and $R^2$ in the general formula (1), $X^3$ represents the same group represented by $X^1$ in the general formula (1), $X^4$ represents the same group represented by $X^2$ in the general formula (1), $R^9$ and $R^{10}$ each independently represents a carboxy group which may be bonded to an alkali metal to form a salt, and $R^{11}$ and $R^{12}$ represent the same groups as those represented by $R^5$ and $R^6$ in the general formula (1)).

In the general formula (2), $R^{11}$ and $R^{12}$ each independently represents a carboxy group, a sulfo group, a nitro group, an amino group, or a hydroxy group, provided that the carboxy group or sulfo group may be bonded to an alkali metal to form a salt. In order to uniformly form an alignment film on the surface of the substrate, a functional group having high affinity with a transparent electrode made of glass or ITO is preferable, and a carboxy group and a sulfo group are more preferable, and a sulfo group is particularly preferable. A compound represented by the general formula (2') in which $R^{11}$ and $R^{12}$ are substituted on the 2- and 2'-positions of the 4,4'-bis(phenylazo)biphenyl backbone is particularly preferable because excellent photo-alignment properties are obtained:

(Method for Producing Photo-alignment Film)

The method for producing a photo-alignment film of the present invention includes the steps of optionally adjusting viscosity of the photo-alignment film composition using the solvent or polymer material, coating the solution of the photo-alignment film composition on a substrate, and aligning the azo compound represented by the general formula (1) (both compounds when an azo compound represented by the general formula (2) is included) through light having anisotropy to obtain a photo-alignment film. When an azo compound having a polymerizable functional group is included, a polymerizable functional group is polymerized by heating or irradiating with light after a photo-aligning treatment.

The substrate used in the present invention is a substrate which is usually used in a liquid crystal display including a photo-alignment film, and particularly preferably a substrate having heat resistance enough to endure heat in the production of a liquid crystal display. Examples of the substrate include substrate made of glass or a heat-resistant polymer.

Usually, the substrate is used in the state of being provided with a transparent electrode made of ITO on the surface thereof. In the present invention, first, the composition for

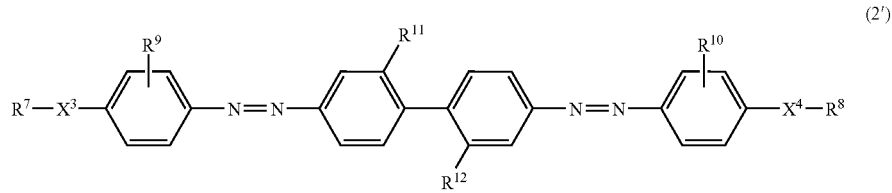

(2')

photo-alignment film of the present invention is coated on a substrate using a method such as a spin coating method, a printing method, a die coating method, or a dipping method, and, after drying, a photo-alignment operation of the resulting coating film is conducted. Among above methods, a printing method is excellent in mass productivity and therefore particularly preferable.

Photo-alignment is conducted by irradiating with light which can serve as light having anisotropy in the coating film. Specifically, the coating film is irradiated with polarized light such as linearly polarized light or elliptically polarized light, or irradiated with unpolarized light from a tilted direction to a film plane.

The polarized light may be linearly polarized light or elliptically polarized light, but is preferably linearly polarized light having a high extinction ratio so as to efficiently conduct photo-alignment.

There is a fear that intensity of polarized light irradiated to the film plane decreases because a polarization filter is used. However, a method of irradiating a film plane with polarized light from a tilted direction has such a merit that an irradiation equipment does not require a polarization filter, large irradiation intensity can be obtained, and also an irradiation time for photo-alignment can be decreased. At this time, an incidence angle of unpolarized light is preferably within a range from 10° to 80° to a glass substrate normal line, and is most preferably from 20° to 60° taking account of uniformity of irradiation energy on the irradiated surface, the resulting pre-tilt angle, and alignment efficiency. Light to be irradiated is light in a range in which the azo compound represented by the general formula (1) has absorption. Specifically, ultraviolet light within a wavelength of 300 to 500 nm in which strong absorption attributed to $\pi \rightarrow \pi^*$ transition of azobenzene is present.

Examples of the light source for light to be irradiated include a xenon lamp, a high-pressure mercury-vapor lamp, an ultrahigh-pressure mercury-vapor lamp, a metal halide lamp, and an ultraviolet laser such as He—Cd laser or YAG laser. An ultrahigh-pressure mercury-vapor lamp is particularly preferable because emission intensity of an ultraviolet light having a wavelength of 365 nm is large, which is closer to a maximum absorption wavelength of the azo compound represented by the general formula (1).

When $R^1$ and $R^2$ of the azo compound represented by the general formula (1) is a polymerizable functional group, in addition to the photo-alignment operation, a polymerization operation is conducted. When the polymerization operation is conducted by thermal polymerization, it is conducted by heating a substrate which was coated with the photo-alignment film composition and then subjected to the photo-alignment operation, as described above. The heating temperature is preferably within a range from 100 to 300° C., and more preferably from 100 to 200° C.

When the polymerization operation is conducted by irradiation with light, it is preferably to irradiate with light having a wavelength, which is not absorbed by an azobenzene backbone, so as not to cause turbulence of an alignment state of already obtained material for photo-alignment film, namely, light having a wavelength which is different from that imparts liquid crystal alignment capability. Specifically, it is preferred to irradiate with unpolarized ultraviolet light having a wavelength of 200 to 320 nm. More stable photo-alignment film is obtained by conducting the polymerization operation and a liquid crystal display capable of maintaining a high voltage-holding ratio by using the photo-alignment film.

(Applications)

The photo-alignment film produced by the composition for photo-alignment film of the present invention is used for the purpose of mainly aligning a liquid crystal composition, and examples thereof will now be described but are not to be considered as limiting.

(Liquid Crystal Display)

A liquid crystal display including a photo-alignment film made of the composition for photo-alignment film of the present invention is produced by a conventionally known method. An example of the method for producing a TN type liquid crystal display will now be described.

On the surface of two glass substrates on which a transparent electrode made of ITO is provided, the composition for photo-alignment film of the present invention is coated and dried, and then an aligning treatment is conducted by means of visible light or ultraviolet light. Then, surfaces of the photo-alignment films are allowed to face each other via a spacer so as to make alignment directions of the respective photo-alignment films to intersect perpendicularly each other, and two substrates are laminated using a sealing material. A liquid crystal is filled into the space between two substrates through a pore opened when laminated using the sealing material. A TN type liquid crystal display can be produced by laminating a polarizing plate on the external side of the resulting liquid crystal cell so that the alignment direction of a photo-alignment film in the respective substrates and the direction of polarized light transmitted agree.

(Optically Anisotropic Body)

An optically anisotropic body can also be produced by aligning a liquid crystal compound having a polymerizable group using a photo-alignment film made of the composition for photo-alignment film of the present invention, followed by polymerization. It is produced by a conventionally known method, and an example thereof will now be described.

For example, on a substrate such as a glass substrate or a plastic substrate, the composition for photo-alignment film of the present invention is coated and dried and then an aligning treatment is conducted by means of visible light or ultraviolet light. On the resulting photo-alignment film, a material such as polymerizable liquid crystal composition capable of forming an optically anisotropic body is coated, or interposed between two substrate followed by polymerization, thereby making it possible to produce an optically anisotropic body.

EXAMPLES

The present invention will now be described in detail by way of examples and comparative examples, but the present invention is not limited thereto. The compounds Nos. are the same as those described in Tables 1 to 4.

Example 1

Synthesis of Compound No. A-1

5.00 g (14.5 mmol) of 2,2'-benzidinedisulfonic acid was dissolved in 70 ml of an aqueous 3.3% (w/v) sodium hydroxide solution, followed by stirring at 0 to 5° C. While maintaining at the same temperature, 2.10 g (30.5 mmol) of sodium nitrite dissolved in 60 ml of water was added, and then 22 ml of an aqueous 8 N hydrochloric acid solution was slowly added dropwise. After the completion of the dropwise addition, stirring was continued for 3 hours while maintaining the temperature of the reaction solution to prepare a diazonium salt. Then, 4.0 g (29.0 mmol) of 2-ethoxyphenol was dissolved in 140 ml of an aqueous 3.5% (w/v) sodium hydroxide solution, followed by cooling to 0 to 5° C., and the diazonium salt mixture obtained by the above method was gradually added dropwise. After the completion of the dropwise addition, stirring was continued for 2.5 hours while maintaining the temperature of the reaction solution. To the reaction solution, 70 g of sodium chloride was added, followed by stirring at room temperature for a while, and the resulting precipitate was removed by filtration to obtain a crude product. The resulting crude product was dried under reduced pressure, washed with heated acetone, and dissolved in 100 ml of heated N,N-dimethylformamide so as to remove insolubles by filtration, and the filtrate was distilled off under reduced pressure to obtain 5.5 g (yield: 55%) of a compound No. A-1.

Example 2

Synthesis of Compound No. A-7

1.50 g (4.35 mmol) of 2,2'-benzidinedisulfonic acid was dissolved in 21 ml of an aqueous 3.3% (w/v) sodium hydroxide solution, followed by stirring at 0 to 5° C. While maintaining at the same temperature, 0.633 g (9.17 mmol) of sodium nitrite dissolved in 15 ml of water was added, and then 6.54 ml of an aqueous 8 N hydrochloric acid solution was slowly added dropwise. After the completion of the dropwise addition, stirring was continued for 3 hours while maintaining the temperature of the reaction solution to prepare a diazonium salt. Then, 1.34 g (8.70 mmol) of 2-(methoxymethoxy)phenol dissolved in 2 ml of tetrahydrofuran was dissolved in 85 ml of an aqueous 5% (w/v) sodium carbonate solution, followed by cooling to 0 to 5° C., and the diazonium salt mixture obtained by the above method was gradually added dropwise. After the completion of the dropwise addition, stirring was continued for 2.5 hours while maintaining the temperature of the reaction solution. To the reaction solution, 28 g of sodium chloride was added, followed by stirring at room temperature for a while, and the resulting precipitate was removed by filtration to obtain a crude product. The resulting crude product was dried under reduced pressure, washed with heated acetone, and dissolved in 50 ml of heated N,N-dimethylformamide so as to remove insolubles by filtration, and the filtrate was distilled off under reduced pressure to obtain 1.9 g (yield: 61%) of a compound No. A-7.

Example 3

Synthesis of Compound No. A-10

2.75 g (3.83 mmol) of the compound No. A-7 obtained in Example 2, 2.24 g (7.67 mmol) of 4-(6-acryloyloxyhexyloxy)benzoic acid, and 1.54 g (8.02 mmol) of 1-ethyl-3-(3'-dimethylaminopropyl)carbodiimide hydrochloride were dissolved in 30 ml of N,N-dimethylformamide, followed by stirring while cooling in an ice bath, and a solution prepared by dissolving 330 mg (2.70 mmol) of 4-(N,N-dimethylamino)pyridine in 5 ml of N,N-dimethylformamide was slowly added. After removing the ice bath and stirring room temperature for 3 hours, the reaction solution was pored into an ice-0.5 N hydrochloric acid water and then extracted with dichloromethane. The organic layer was washed with semisaturated saline and then dried over anhydrous magnesium sulfate. The organic layer was removed by filtration, and the filtrate was concentrated under reduced pressure to obtain a residue, which was then purified by silica gel column chromatography (eluant: dichloromethane/methanol/acetic acid=40/1/1 to 20/1/1). A fraction containing an objective product was collected, washed with water, and washed with saturated sodium hydrogen carbonate, and then the solvent was distilled off under reduced pressure. The resulting residue was washed with n-hexane to obtain 2.2 g (yield: 45%) of a compound No. A-10.

Example 4

Synthesis Compound No. A-8

In the same manner as in Example 3, the esterification reaction was conducted to obtain a compound No. A-8 from the compound No. A-1 obtained in Example 1 and 4-(6-acryloyloxyhexyloxy)benzoic acid.

Example 5

Synthesis of Compound No. B-1

3.00 g (8.71 mmol) of 2,2'-benzidinedisulfonic acid was dissolved in 42 ml of an aqueous 3.3% (w/v) sodium hydroxide solution, followed by stirring at 0 to 5° C. While maintaining at the same temperature, 1.26 g (18.3 mmol) of sodium nitrite dissolved in 36 ml of water was added, and then 13.1 ml of an aqueous 8 N hydrochloric acid solution was slowly added dropwise. After the completion of the dropwise addition, stirring was continued for 3 hours while maintaining the temperature of the reaction solution to prepare a diazonium salt. Then, 2.16 g (17.4 mmol) of 2-hydroxymethylphenol was dissolved in 90 ml of an aqueous 3.3% (w/v) sodium hydroxide solution, followed by cooling to 0 to 5° C., and the diazonium salt mixture obtained by the above method was gradually added dropwise. After the completion of the dropwise addition, stirring was continued overnight while maintaining the temperature of the reaction solution. To the reaction solution, 50 g of sodium chloride was added, and the pH of the solution was adjusted to 1 by adding concentrated hydrochloric acid, followed by stirring for a while at room temperature. The resulting precipitate was removed to obtain a crude product. The resulting crude product was dried under reduced pressure, washed with heated acetone, and dissolved in 100 ml of heated N,N-dimethylformamide so as to remove insolubles by filtration, and the filtrate was distilled off under reduced pressure. Furthermore, the concentrated residue was washed with heated tetrahydrofuran to obtain 4.6 g (yield: 80%) of a compound No. B-1.

Example 6

Synthesis of Compound No. B-8

1.02 g (3.50 mmol) of 4-(6-acryloyloxyhexyloxy)benzoic acid was dissolved in 10 ml of toluene, and 0.33 ml of oxalyldichloride and then one drop of N,N-dimethylformamide was added under ice cooling while stirring. After removing an ice bath and stirring at room temperature for 2 hours, toluene was distilled off under reduced pressure to prepare 4-(6-acryloyloxyhexyloxy)benzoic acid chloride. 1.00 g (1.52 mmol) of the compound No. B-1 obtained in Example 6 was suspended in 50 ml of pyridine, and a solution prepared by dissolving the acid chloride prepared by the above method in 3.0 ml of tetrahydrofuran was added at room temperature. After stirring at room temperature for 4 hours, the reaction solution was poured into an aqueous 1 N hydrochloric acid, followed by extraction with dichloromethane. The organic layer was washed in turn with an aqueous 2 N hydrochloric acid and water, and then dried over anhydrous magnesium sulfate. The organic layer was filtered, and the solvent was distilled off under reduced pressure, and then the residue was purified by silica gel column chromatography (eluant: dichloromethane/methanol/acetic acid=20/1/1 to 10/1/1). A fraction containing the objective product was washed with water, and the solvent was distilled off under reduced pressure to obtain 0.70 g (yield: 38%) of a compound B-8.

Example 7

Synthesis of Compound No. C-7

10.0 g (65.7 mmol) of methyl salicylate and 33 ml of n-butylamine were dissolved in 100 ml of methanol, followed by heating at reflux for 8 hours while stirring. Methanol was distilled off under reduced pressure, and the residue was acidified by adding an aqueous 2 N hydrochloric acid, followed by extraction with dichloromethane. The organic layer was washed in turn with water and saturated sodium hydrogen carbonate, and then dried over anhydrous magnesium sulfate. The organic layer was filtered, and the filtrate was concentrated under reduced pressure, and then the resulting residue was purified by silica gel column chromatography (eluant hexane/ethyl acetate=10/1 to 5/1) to obtain 10.0 g (yield: 79%) of salicylic acid n-butylamide as an oily substance. $^1$H—NMR spectrum data of salicylic acid n-butylamide are as follows.

$^1$H—NMR (CDCl$_3$) δppm: 0.97 (t, J=7.5Hz, 3H), 1.42 (m, 2H), 1.61 (m, 2H), 3.45 (m, 2H), 6.31 (brd, 1H), 6.84 (ddd, J=1.0, 6.8, 8.3 Hz, 1H), 6.98 (dd, J=1.5, 8.3 Hz, 1H), 7.37 (m, 2H), 12.4 (s, 1H).

On the other hand, 2.00 g (5.81 mmol) of 2,2'-benzidinedisulfonic acid was dissolved in 28 ml of an aqueous 3.3% (w/v) sodium hydroxide solution, followed by stirring at 0 to 5° C. While maintaining at the same temperature, 0.843 g (12.2 mmol) of sodium nitrite dissolved in 24 ml of water was added, and 8.7 ml of an aqueous 8 N hydrochloric acid solution was slowly added dropwise. After the completion of the dropwise addition, stirring was continued for 3 hours while maintaining the temperature of the reaction solution to prepare a diazonium salt. Then, 2.24 g (11.6 mmol) of salicylic acid n-butylamide synthesized by the above method was dissolved in 60 ml of an aqueous 3.3% (w/v) sodium hydroxide solution, followed by cooling to 0 to 5° C., and the diazonium salt mixture obtained by the above method was gradually added dropwise while stirring. After the completion of the dropwise addition, stirring was continued overnight while maintaining the temperature of the reaction solution. To the reaction solution, 35 g of sodium chloride was added at room temperature, followed by stirring at room temperature for a while, and the resulting precipitate was removed by filtration to obtain a crude product. The resulting crude product was dried under reduced pressure, washed with heated acetone, and dissolved in 40 ml of heated N,N-dimethylformamide so as to remove insolubles by filtration, and the filtrate was distilled off under reduced pressure to obtain 3.8 g (yield: 82%) of a compound No. C-7.

Example 8

Synthesis of Compound No. C-1

In the same manner as in Example 7, a compound No. C-1 was obtained from 2,2'-benzidinedisulfonic acid and salicylic acid amide.

Example 9

Synthesis of Compound No. C-5

In the same manner as in Example 7, a compound No. C-5 was obtained from 2,2'-benzidinedisulfonic acid and salicylic acid N,N'-dimethylamide.

$^1$H—NMR spectrum data of the azo compounds Nos. A-1, A-7, A-8, A-10, B-1, B-8, C-1, C-5, and C-7 produced in these examples were summarized in Table 5.

TABLE 5

| Compound No. | $^1$H-NMR (dimethyl sulfoxide-d6) δ ppm |
|---|---|
| A-1 | 1.38 (t, J=6.8 Hz, 6H), 4.14 (q, J=6.8 Hz, 4H), 6.98 (d, J=7.8 Hz, 2H), 7.4 to 7.55 (m, 6H), 7.69 (dd, J=2.0, 8.3 Hz, 2H), 8.31 (d, J=2.0 Hz, 2H) |
| A-7 | 3.46 (s, 6H), 5.27 (s, 4H), 6.98 (d, J=8.3 Hz, 2H), 7.45 (d, J=8.3 Hz, 2H), 7.54 (dd, J=2.4, 8.3 Hz, 2H), 7.62 (d, J=2.4 Hz, 2H), 7.68 (dd, J=2.0, 8.3 Hz, 2H), 8.30 (d, J=2.0 Hz, 2H) |
| A-8 | 1.3 to 1.55 (m, 14H), 1.65 (m, 4H), 1.76 (m, 4H), 4.13 (m, 12H), 5.94 (dd, J=1.8, 10.0 Hz, 2H), 6.18 (dd, J=10.0, 17.0 Hz, 2H), 6.33 (dd, J=1.8, 17.0 Hz, 2H), 7.15 (d, J=8.8 Hz, 4H), 7.52 (d, J=8.2 Hz, 2H), 7.61 (d, J=8.0 Hz, 2H), 7.73 (dd, J=2.1, 8.2 Hz, 2H), 7.85 (m, 4H), 8.12 (d, J=8.8 Hz, 4H), 8.50 (d, J=2.5 Hz, 2H) |
| A-10 | 1.30 to 1.55 (m, 8H), 1.66 (m, 4H), 1.78 (m, 4H), 3.38 (s, 6H), 4.13 (m, 8H), 5.34 (s, 4H), 5.94 (dd, J=1.8, 10.1 Hz, 2H), 6.18 (dd, J=10.1, 17.2 Hz, 2H), 6.33 (dd, J=1.8, 17.2 Hz, 2H), 7.14 (d, J=8.9 Hz, 4H), 7.52 (d, J=8.4 Hz, 2H), 7.60 (d, J=8.1 Hz, 2H), 7.72 (dd, J=2.2, 8.4 Hz, 2H), 7.83 (m, 4H), 8.12 (d, J=8.9 Hz, 4H), 8.43 (d, J=2.6 Hz, 2H) |
| B-1 | 4.55 (s, 4H), 6.97 (d, J=8.7 Hz, 2H), 7.49 (d, J=8.1 Hz, 2H), 7.71 (dd, J=2.2, 8.1 Hz, 2H), 7.74 (dd, J=2.5, 8.7 Hz, 2H), 7.97 (d, J=2.5 Hz, 2H), 8.31 (d, J=2.2 Hz, 2H), 10.3 (brd, 2H) |
| B-8 | 1.3 to 1.55 (m, 8H), 1.66 (m, 4H), 1.76 (m, 4H), 4.13 (m, 8H), 4.58 (s, 4H), 5.94 (dd, J=1.8, 10.3 Hz, 2H), 6.18 (dd, J=10.3, 17.2 Hz, 2H), 6.32 (dd, J=1.8, 17.2 Hz, 2H), 7.15 (d, J=8.8 Hz, 4H), 7.49 (d, J=8.4 Hz, 2H), 7.60 (d, J=7.7 Hz, 2H), 7.85 (dd, J=2.2, 7.7 Hz, 2H), 7.95 (d, J=8.4 Hz, 2H), 8.13 (m, 6H), 8.43 (d, J=2.2 Hz, 2H) |
| C-1 | 6.68 (d, J=8.8 Hz, 2H), 7.36 (brd, 2H), 7.41 (d, J=8.3 Hz, 2H), 7.64 (dd, J=2.4, 8.3 Hz, 2H), 7.80 (dd, J=2.4, 8.8 Hz, 2H), 8.28 (d, J=2.4 Hz, 2H), 8.46 (d, J=2.4 Hz, 2H), 9.87 (brd, 2H) |
| C-5 | 2.9 (brd, 6H), 7.08 (d, J=8.8 Hz, 2H), 7.50 (d, J=8.2 Hz, 2H), 7.72 (m, 4H), 7.88 (dd, J=2.4, 8.8 Hz, 2H), 8.32 (d, J=2.4 Hz, 2H) |
| C-7 | 0.92 (t, J=7.1 Hz, 6H), 1.3 to 1.55 (m, 8H), 3.29 (m, 4H), 6.35 (d, J=9.2 Hz, 2H), 7.55 (dd, J=2.3, 8.0 Hz, 2H), 7.63 (dd, J=2.9, 9.2 Hz, 2H), 8.21 (d, J=2.3 Hz, 2H), 8.33 (d, J=2.9 Hz, 2H) |

Synthesis Examples of compounds represented by the general formula (2) used in a composition for photo-alignment film are shown below.

Synthesis Example 1

Synthesis of Compound (a)

To 8.6 g (25 mmol) of 2,2'-benzidinedisulfonic acid, 230 ml of 2% hydrochloric acid was added, and an aqueous solution of 3.5 g (51 mmol) of sodium nitrite was gradually added dropwise while maintaining at 0 to 5° C., followed by the reaction for 2 hours to prepare a diazonium salt. Then, 6.9 g (50 mmol) of salicylic acid was dissolved in 300 ml of an aqueous 5% sodium carbonate solution, and the diazonium salt mixture was gradually added dropwise thereto. After reacting for one hour, 20% saline was added to obtain a precipitate. The resulting precipitate was recrystallized from a solvent mixture of ethanol and water to obtain 4.8 g of an azo compound represented by the formula (a):

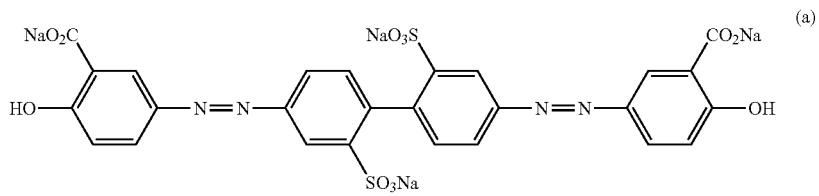

(a)

Synthesis Example 2

Synthesis of Compound (b)

5.17 g (15.0 mmol) of 2,2'-benzidinedisulfonic acid was dissolved in 75 ml of an aqueous 3.3% (w/v) sodium hydroxide solution, followed by stirring at 0 to 5° C. While maintaining at the same temperature, 2.28 g (33.0 mmol) of sodium nitrite dissolved in 65 ml of water was added, and then 22.5 ml of an aqueous 8N hydrochloric acid solution was slowly added dropwise. After the completion of the dropwise addition, stirring was conducted for 3 hours while maintaining the temperature of the reaction solution to prepare a diazonium salt. Then, 4.87 g (30.0 mmol) of o-trifluoromethylphenol was dissolved in 150 ml of an aqueous 3.3% (w/v) sodium hydroxide solution, followed by cooling to 0 to 5° C., and the diazonium salt mixture obtained by the above method was gradually added dropwise while stirring. After the completion of the dropwise addition, stirring was continued overnight while maintaining the temperature of the reaction solution. To the reaction solution, 75 g of sodium chloride was added, followed by stirring at room temperature for a while, and the resulting precipitate was removed by filtration to obtain a crude product. The resulting crude product was dried under reduced pressure and washed with heated acetone to obtain 6.1 g of an azo compound represented by the formula (b). Then, the azo compound was recrystallized from a solvent mixture of ethanol and ethyl acetate.

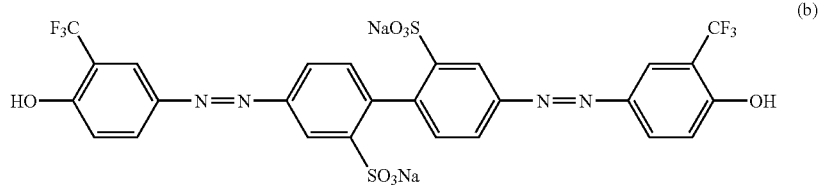

(b)

Synthesis Example 3

Synthesis of Compound (c)

After 2.0 g of p-anise alcohol was reacted with 2.0 g of acetyl bromide in dichloromethane, the solvent was distilled off. 2.5 g of the resulting compound was dissolved in N,N-dimethylformamide, and 1.6 g of the compound represented by the formula (a) was added thereto, followed by the reaction in the presence of triethylamine. Then, 0.6 g of 4-(6-acryloyloxyhexyloxy)benzoic acid was added, followed by the reaction in the presence of 1-ethyl-3-(3'-dimethylaminopropyl)carbodiimide hydrochloride. After the solvent was distilled off, the resulting crude product was dissolved in anisole, and trifluoroacetic acid was added, followed by the reaction. Finally, the solvent was distilled off, followed by washing with hexane to obtain 0.1 g of an azo compound represented by the formula (c):

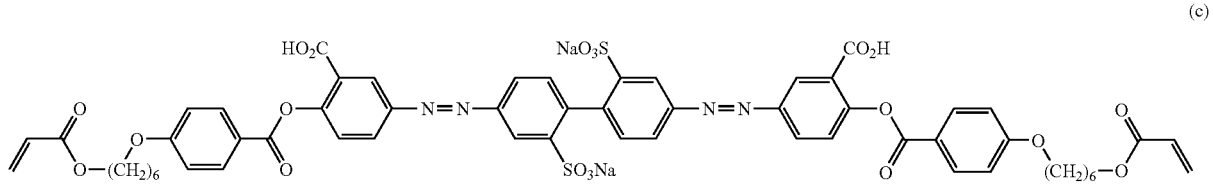

(c)

Synthesis Example 4

Synthesis of Compound (d)

2.00 g (2.70 mmol) of the compound represented by the formula (b), 1.74 g (5.94 mmol) of 4-(6-acryloyloxyhexyloxy)benzoic acid, and 1.30 g (6.77 mmol) of 1-ethyl-3-(3'-dimethylaminopropyl)carbodiimide hydrochloride were dissolved in 20 ml of N-dimethylformamide and stirred while cooling in an ice bath, and then a solution prepared by dissolving 230 mg (1.89 mmol) of 4-(N,N-dimethylamino)pyridine in 4 ml of N,N-dimethylformamide was slowly added. After removing the ice bath and stirring at room temperature for 3 hours, the reaction solution was poured into ice-aqueous 1N hydrochloric acid, followed by extraction with dichloromethane. The organic layer was washed in turn with water, saturated sodium hydrogen carbonate, and saturated saline, and then dried over anhydrous magnesium sulfate. The organic layer was filtered, and the filtrate was concentrated under reduced pressure, and then the resulting residue was purified by silica gel column chromatography (eluant: dichloromethane/methanol/acetic acid=40/1/1 to 20/1/1). A fraction containing the objective product was collected, washed with water, and washed with saturated sodium hydrogen carbonate, and then the solvent was distilled off under reduced pressure. The residue was washed with n-hexane to obtain 1.6 g of an azo compound represented by the formula (d):

solved in 49.5 parts by weight of N-methyl-2-pyrrolidone and 49.5 parts by weight of 2-butoxyethanol. The resulting solution was pressure-filtered through a membrane filter having a pore size of 0.45 µm to obtain a solution for a photo-alignment film. The resulting solution for a photo-alignment film was coated on a glass substrate with an ITO electrode using a spin coater, and then dried at 100° C. for one minute. The surface of the resulting coating film was irradiated with ultraviolet parallel light having a wavelength of about 365 nm from an angle of 45° diagonally with the glass substrate through a band pass filter using an ultrahigh-pressure mercury vapor lamp. The exposure amount was 5 J/cm² in terms of integrated light quantity. The photo-alignment film thus obtained was thermally polymerized by heating under a nitrogen atmosphere at 150° C. for one hour.

(Production of TN Liquid Crystal Cell)

An epoxy-based adhesive containing silica beads having a diameter of 10 µm (manufactured by Mitsui Chemicals under the trade name of "Struct Bond XN-5A") was coated on the peripheral surface of a photo-alignment film of a glass substrate with a photo-alignment film, excluding a liquid crystal filling port. After preliminarily curing at 80° C. for 30 minutes, another glass substrate with a photo-alignment film, which is not coated with an adhesive, was laid so that alignment surfaces are perpendicularly intersected each other, followed by contact bonding and further curing at 150° C. for 90 minutes. Subsequently, a liquid crystal composition for driving TFT (manufactured by Dainippon Ink and Chemicals, Inc. under the trade name of "11-3323") was poured from a liquid crystal filling port under vacuum, and then the liquid crystal filling port was sealed with an epoxy-based adhesive to obtain TN liquid crystal cells for evaluation. In order to stabilize alignment properties of the liquid crystal, the TN liquid crystal cells for evaluation were heated to the temperature higher than a transition temperature of the liquid crystal, and then slowly cooled to room temperature, and then subjected to evaluation.

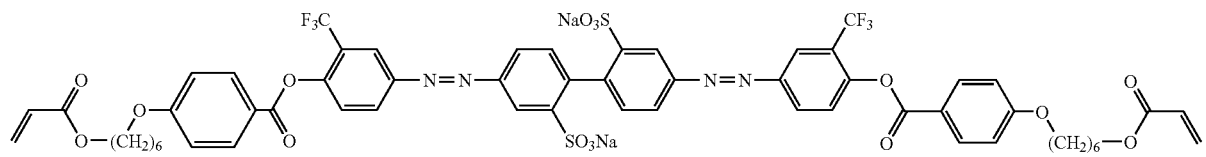

(d)

Examples 10 to 18

Method for Producing Glass Substrate With Photo-Alignment Film

With respect to Examples 10 to 15, photo-alignment films were produced by the following method using compounds Nos. A-1, A-7, B-1, C-1, C-5, and C-7.

1.0 Parts by weight of each compound was dissolved in 49.5 parts by weight of N-methyl-2-pyrrolidone and 49.5 parts by weight of 2-butoxyethanol. The resulting solution was pressure-filtered through a membrane filter having a pore size of 0.45 µm to obtain a solution for a photo-alignment film. The resulting solution for a photo-alignment film was coated on a glass substrate with an ITO electrode using a spin coater, and then dried at 100° C. for one minutes. The surface of the resulting coating film was irradiated with ultraviolet parallel light having a wavelength of about 365 nm from an angle of 45° diagonally with the glass substrate through a band pass filter using an ultrahigh-pressure mercury vapor lamp. The exposure amount was 5 J/cm² in terms of integrated light quantity.

With respect to Examples 16 to 18, photo-alignment films were produced by the following method using compounds Nos. A-8, A-10, and B-8.

1.0 Parts by weight of each compound and 0.025 parts by weight of a photopolymerization initiator V-40 (manufactured by Wako Pure Chemicals Industries, Ltd.) were dis- (Method for Evaluation of Photo-Alignment Film)

(Liquid Crystal Alignment Properties)

For evaluation of liquid crystal alignment properties, a polarizing microscope equipped with a photomultiplier under cross-nicol condition was used. Assumed that a light transmittance when light from a tungsten lamplight source of the polarizing microscope was completely shielded is 0% and that a light transmittance when a polarizing plate is applied on parallel-nicol in the state where a sample is not placed on a sample stage is 100%, an output from the photomultiplier was reduced. The TN liquid crystal cells were arranged in the direction in which the light transmittance increases most remarkably in the state where no voltage is applied, and then a voltage of 0 to 5 V was applied between electrodes of the TN liquid crystal cells, followed by sweeping, thereby obtaining a voltage-light transmittance (V-T) curve. Liquid crystal alignment properties were evaluated by a contrast ratio represented by the following formula and also visually evaluated.

Contrast ratio=light transmittance when 4 V is applied/light transmittance when 0 V is applied (measured at room temperature)

Visual Evaluation
A: exhibit good alignment uniformly in one direction
B: exhibit good alignment, but is inferior to A
C: exhibit partial alignment, but defects exist
D: exhibit no alignment (evaluated at room temperature)

ment properties, voltage-holding ratio, and thermal endurance were evaluated.

(Evaluation Results)

The evaluation results of the liquid crystal alignment properties, voltage-holding ratio, and thermal endurance are shown in Table 6. As is apparent from the results shown in Table 6, the TN liquid crystal cells of the examples exhibit good alignment properties, good voltage-holding ratio, and good thermal endurance.

TABLE 6

| Examples | Compound No. | Liquid crystal alignment properties Contrast ratio | Liquid crystal alignment properties (visual) | | Voltage-holding ratio (%) | | Change in voltage-holding ratio (%) |
|---|---|---|---|---|---|---|---|
| | | | Initial | After thermal endurance test | Initial | After thermal endurance test | |
| Example 10 | A-1 | 89.5 | A | A | 93.2 | 92.3 | −0.97 |
| Example 11 | A-7 | 91.2 | A | A | 83.3 | 82.9 | −0.48 |
| Example 12 | B-1 | 92.4 | A | A | 90.5 | 90.1 | −0.44 |
| Example 13 | C-1 | 89.4 | B | B | 96.5 | 95.9 | −0.62 |
| Example 14 | C-5 | 88.3 | B | B | 93.2 | 92.9 | −0.32 |
| Example 15 | C-7 | 88.5 | B | B | 95.8 | 95.4 | −0.42 |
| Example 16 | A-8 | 88.2 | B | B | 96.1 | 96.2 | −0.10 |
| Example 17 | A-10 | 89.3 | A | A | 94.3 | 94.1 | −0.21 |
| Example 18 | B-8 | 88.9 | A | A | 95.4 | 95.2 | −0.21 |
| Comparative Example 1 | (a) | 94.5 | A | A | 81.2 | 78.5 | −3.33 |
| Comparative Example 2 | (b) | 91.3 | A | A | 21.1 | 18.5 | −12.32 |
| Comparative Example 3 | (c) | 89.9 | B | B | 37.2 | 30.3 | −18.55 |
| Comparative Example 4 | (d) | 87.5 | C | C | 89.2 | 89.1 | −0.11 |

(Voltage-Holding Ratio)

A voltage ratio of the voltage, measured after applying DC voltage 5 V to TN liquid crystal cells for evaluation for 64 micro-seconds and opening a circuit for 200 milli-seconds, to an initial applied voltage was measured (measuring temperature: 25° C.).

(Thermal Endurance)

TN liquid crystal cell for evaluation were allowed to stand at 80° C. for 1000 hours, and alignment properties were visually evaluated, and also a voltage-holding ratio was measured. A voltage-holding ratio was measured by the above evaluation procedure. A change rate relative to an initial value calculated from a difference in a voltage-holding ratio before and after a thermal endurance test was used as an indicator for evaluation of thermal endurance.

Comparative Examples 1 to 4

With respect to Comparative Examples 1 to 2, TN liquid crystal cells were produced in the same manner as in Example 10, except that each of the compounds represented by the formulas (a) and (b) was used. With respect to Comparative Examples 3 to 4, TN liquid crystal cells were produced in the same manner as in Example 16, except that each of the compounds represented by the formulas (c) and (d) was used.

With respect to the TN liquid crystal cells of the respective examples and comparative examples, the liquid crystal align- Examples of a composition containing a compound represented by the general formula (1) and a compound represented by the general formula (2) are shown below.

Examples 19 to 23 and Comparative Examples 6 to 9

Details of examples and comparative examples using an azo compound (1-1) represented by the general formula (1) wherein $R^3$ and $R^4$ represent —$CONR^8R^9$ (wherein $R^8$ and $R^9$ each independently represents a hydrogen atom or an alkyl group having 1 to 6 carbon atoms) in combination with an azo compound represented by the general formula (2) are shown below.

0.3 Parts of a compound No. C-1 as the azo compounds (1-1) and (1-1'), and 0.7 parts of a compound represented by the formula (a) as the compound represented by the general formula (2) were dissolved in 49.5 parts of N-methyl-2-pyrrolidone (NMP), and 49.5 parts of 2-butoxyethanol was added to prepare a solution having a solid content of 1.0%. The resulting solution was filtered through a membrane filter having a pore size of 0.45 µm to obtain a composition for a photo-alignment film (1). Using a compound No. C-1, a compound represented by the formula (a), and a compound No. C-7, compositions for photo-alignment films (2) to (9) were produced according to a mixing ratio shown in Table 7.

Each of the resulting compositions for photo-alignment films (1) to (9) was coated on a glass substrate using a spin coater and then dried at 100° C. for one minute. The surface of the resulting coating film was irradiated with light according to the following irradiation conditions A and B to obtain a photo-alignment film. With respect to the resulting photo-alignment film, liquid crystal alignment capability (order parameter, alignment minimum dose) was evaluated by the following evaluation procedure. The results are shown in Table 7.

ment film produced at an integrated light quantity of 200 mJ was used. An absorbance to linearly polarized light having a maximum absorption wavelength of the glass substrate with a photo-alignment film was measured, and an order parameter was calculated from the following equation (1):

TABLE 7

| Compound No. | Example 19 | Example 20 | Example 21 | Example 22 | Example 23 | Comparative Example 6 | Example 24 | Example 25 | Example 26 |
|---|---|---|---|---|---|---|---|---|---|
| Composition for photo-alignment film | (1) | (2) | (3) | (4) | (5) | (6) | (7) | (8) | (9) |
| (a) | 0.7 | 0.55 | 0.95 | 0.9 | 0.9 | 1 | | | 0.4 |
| C-1 | 0.3 | 0.45 | 0.05 | 0.1 | | | 1 | | 0.6 |
| C-7 | | | | | 0.1 | | | 1 | |
| Irradiation condition A | | | | | | | | | |
| (Order parameter) | −0.07 | −0.061 | −0.075 | −0.078 | −0.082 | −0.051 | −0.019 | −0.015 | −0.039 |
| (Alignment minimum dose) | 60 | 80 | 60 | 40 | 20 | 100 | >200 | >200 | 200 |
| Irradiation condition B | | | | | | | | | |
| (Order parameter) | −0.029 | −0.024 | −0.038 | −0.039 | −0.042 | −0.022 | −0.012 | −0.01 | −0.015 |
| (Alignment minimum dose) | 200 | 250 | 200 | 150 | 150 | 300 | >500 | >500 | >500 |

(Light Irradiation Conditions)

(Irradiation Condition A)

Linear polarized and parallel light of visible ultraviolet light having a wavelength of about 300 to 500 nm (irradiation energy: 20 mW/cm$^2$, integrated light quantity: 20, 40, 60, 80, 100, 150, or 200 mJ) was irradiated from the direction perpendicular to a glass substrate through a wavelength cut filter and a polarization filter using an ultrahigh-pressure mercury vapor lamp to obtain a photo-alignment film.

(Irradiation Condition B)

Parallel light of unpolarized visible ultraviolet light having a wavelength of about 300 to 500 nm (irradiation energy: 50 mW/cm$^2$, integrated light quantity: 50, 100, 150, 200, 250, 300, 400, or 500 mJ) was irradiated from an angle of 45° diagonally with a glass substrate through a wavelength cut filter using an ultrahigh-pressure mercury vapor lamp to obtain a photo-alignment film.

(Evaluation Procedure)

(Order Parameter)

An order parameter was calculated from an absorbance, and anisotropy and its direction of a photo-alignment film were evaluated. A polarization visible ultraviolet spectrophotometer was used for the measurement of an absorbance. The larger an absolute value of an order parameter S, the more alignment capability of a liquid crystal becomes higher. The order parameter shows a positive value when an azo compound is aligned in parallel to the direction of polarized light irradiated on an alignment film, while the order parameter shows a negative value when the azo compound is aligned in perpendicular to the direction of polarized light irradiated on the alignment film. In the irradiation condition A, a photo-alignment film produced at an integrated light quantity of 100 mJ was used. In the irradiation condition B, a photo-align-

[Equation 1]

$$S = \frac{A_{\|} - A_{\perp}}{A_{\|} + 2A_{\perp}} \quad (1)$$

(wherein, A ∥ denotes an absorbance when the polarization direction of ultraviolet light irradiated for alignment of a photo-alignment film is in parallel to the direction of polarized light which is incident for measurement of an absorbance, and A⊥ denotes an absorbance when the polarization direction of ultraviolet light irradiated for alignment of a photo-alignment film is in perpendicular to the direction of polarized light which is incident for measurement of an absorbance).

(Alignment Minimum Dose)

An epoxy-based adhesive containing silica beads having a diameter of 10 μm (manufactured by Mitsui Chemicals under the trade name of "Struct Bond XN-5A") was coated on the peripheral surface of a photo-alignment film of a glass substrate with a photo-alignment film, excluding a liquid crystal filling port. After preliminarily curing at 80° C. for 30 minutes, another glass substrate, which is not coated with an adhesive, was laid so that alignment surfaces are perpendicularly intersected each other, followed by contact bonding and further curing at 150° C. for 90 minutes. Subsequently, a liquid crystal composition for driving TFT (manufactured by Dainippon Ink and Chemicals, Inc. under the trade name of "11-3323") was poured from a liquid crystal filling port under vacuum, and then the liquid crystal filling port was sealed with an epoxy-based adhesive to obtain TN liquid crystal cells for evaluation.

In the irradiation condition A, TN liquid crystal cells were produced using a photo-alignment film produced at an integrated light quantity of 20, 40, 60, 80, 100, 150, or 200 mJ. In the irradiation condition B, TN liquid crystal cells were produced using a photo-alignment film produced at an integrated light quantity of 50, 100, 150, 200, 250, 300, 400, or 500 mJ. In the irradiation condition A, the integrated light quantity of 100 mJ or less is a target value. In the irradiation condition B, the integrated light quantity of 300 mJ or less is a target value.

A glass substrate with no photo-alignment film was laminated on a glass substrate by the above method. Assumed that a light transmittance at 400 to 700 nm in the state where a polarizing plate is applied on parallel-nicol is 100%, a light transmittance in the case of a cross-nicol of the resulting TN liquid crystal cells and a light transmittance in the case of a parallel-nicol were measured using a visible ultraviolet spectrophotometer. Integrated light quantity of a photo-alignment film produced at the smallest integrated light quantity among TN evaluation cells in which a difference in light transmittance is 90% or more was taken as an alignment minimum dose.

As is apparent from these results, the photo-alignment films produced by using the compound No. C-1 and the compound No. C-7 alone as the azo compound (1-1) exhibit excellent alignment properties and high voltage-holding ratio even at high temperature as shown in Table 6. Comparing Examples 24 and 25 with Examples 19 to 23, the photo-alignment films of Examples 19 to 23 obtained by mixing a compound represented by the formula (a) as the compound represented by the general formula (2) with an azo compound (1-1) have improved sensitivity to photo-alignment properties, and a liquid crystal can be aligned at a small dose. These photo-alignment films are excellent as compared with the photo-alignment film of Comparative Example 6 obtained by using the compound (a) alone. Also, it becomes apparent that the photo-alignment films of Examples 19 to 23 (0.05 to 0.45) exhibit higher sensitivity than that of the photo-alignment film of Example 26 which contains the azo compound (1-1) in the proportion of 0.6 based on the sum of the content of an azo compound (1) and a compound represented by the general formula (2). In Examples 19 to 23, an absolute value of an order parameter could be adjusted to more than 0.02 at an alignment minimum dose of 80 mJ or less in the irradiation condition A, or an alignment minimum dose of 250 mJ or less in the irradiation condition B.

FIG. 1 is a graph showing a relation between a value of a ratio of the content of a compound represented by the general formula (1-1) to the sum of the content of a compound represented by the general formula (1-1) and the content of a compound represented by the general formula (2), (content of the compound represented by the general formula (1-1)/(content of the compound represented by the general formula (1-1)+content of the compound represented by the general formula (2)), as a "composition ratio", and an order parameter. Also, FIG. 2 is a graph showing a relation between the "composition ratio", and an alignment minimum dose.

Figure 2:
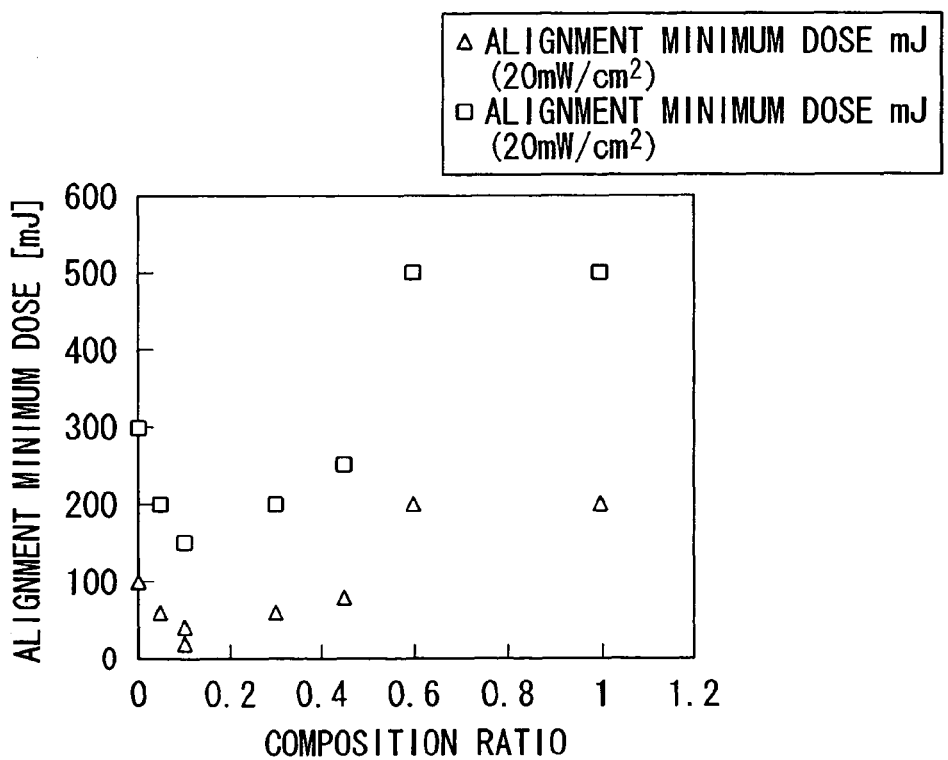
FIG. 2 is a graph showing a relation between a value of a ratio of the content of a compound represented by the general formula (1-1) to the sum of the content of a compound represented by the general formula (1-1) and the content of a compound represented by the general formula (2), as a "composition ratio", and an alignment minimum dose.

As is apparent from FIG. 1 and FIG. 2, when the "composition ratio" is within a range from 0.02 to 0.5, the order parameter is 0.02 or more, and also the alignment minimum dose was 100 mJ or less in terms of an integrated light quantity in the irradiation condition A, and was 300 mJ or less in terms of an integrated light quantity in the irradiation condition B, and thus all target values were achieved.

INDUSTRIAL APPICABILITY

According to the azo compound of the present invention, since the azo compound is easily aligned in a fixed direction to a polarization plane or an incidence plane by irradiation with light having anisotropy such as polarized light or incident light from a tilted direction to a film plane, and thus a film having high anisotropy in the plane and a high alignment-regulating force is obtained. The resulting alignment film exhibits a high voltage-holding ratio. Therefore, the alignment film is industrially useful.

The invention claimed is:

1. An azo compound represented by a general formula (1):

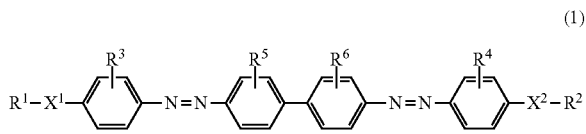

(1)

(wherein, $R^1$ and $R^2$ each independently represents a hydroxy group, or a polymerizable functional group selected from the group consisting of a (meth)acryloyl group, a (meth)acryloyloxy group, a (meth)acrylamide group, a vinyl group, a vinyloxy group, and a maleimide group; $X^1$ represents single bond when $R^1$ is a hydroxy group and represents a linking group represented by $-(A^1-B^1)_m-$ when $R^1$ is a polymerizable functional group; $X^2$ represents a single bond when $R^2$ is a hydroxy group and represents a linking group represented by $-(A^2-B^2)_n-$ when $R^2$ is a polymerizable functional group, wherein $A^1$ is bonded to $R^1$, $A^2$ is bonded to $R^2$, and $B^1$ and $B^2$ each is bonded to an adjacent phenylene group; $A^1$ and $A^2$ each independently represents a single bond, or a phenylene or arylene group which may have a linear alkylene group having 1 to 18 carbon atoms, a branched alkylene group having 1 to 18 carbon atoms, or a linear or branched alkoxy group having 1 to 18 carbon atoms; $B^1$ and $B^2$ each independently represents a single bond, —O—, —CO—O—, —O—CO—, —CO—NH—, —NH—CO—, —NH—CO—O—, or —O—CO—NH—; m and n each independently represents an integer of 0 to 4, provided that a plurality of $A^1$(s), $B^1$(s), $A^2$(s) and $B^2$(s) is the same or different when m or n is 2 or more, $A^1$ or $A^2$ interposed between two $B^1$(s) or $B^2$(s) is not a single bond, and a combination of $A^1$ and $B^1$ or a combination of $A^2$ and $B^2$ is not a combination of only a linear alkylene group and —O—; $R^3$ and $R^4$ each independently represents —$OR^7$ (wherein, $R^7$ represents an alkyl group having 2 to 6 carbon atoms, a cycloalkyl group having 3 to 6 carbon atoms, or an alkyl group having 1 to 6 carbon atoms substituted with a lower alkoxy group having 1 to 6 carbon atoms), a hydroxyalkyl group having 1 to 4 carbon atoms, or —$CONR^8R^9$ (wherein, $R^8$ and $R^9$ each independently represents a hydrogen atom or an alkyl group having 1 to 6 carbon atoms); and $R^5$ and $R^6$ each independently represents a carboxy group, a sulfo group, a nitro group, amino group, or a hydroxy group, provided that a carboxy group and a sulfo group may be bonded to an alkali metal to form a salt).

2. The azo compound according to claim 1, wherein the general formula (1) is represented by the general formula (1'):

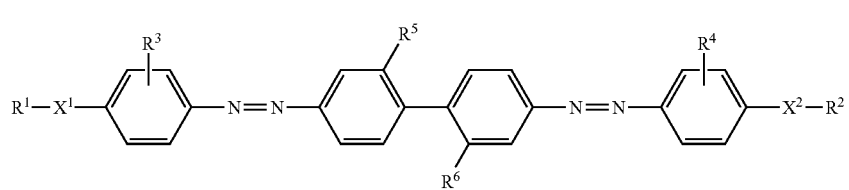

(1')

(wherein, $R^1$ to $R^6$, and $X^1$ and $X^2$ represent the same groups as those represented by the general formula (1)).

3. The azo compound according to claim 2, wherein $R^5$ and $R^6$ represent a sulfo group or a salt thereof in the general formula (1').

4. A composition for a photo-alignment film comprising an azo compound according to claim 1 represented by the general formula (1).

5. The composition for the photo-alignment film according to claim 4, comprising:
   an azo compound (1-1) represented by the general formula (1) in which at least one of $R^3$ and $R^4$ represents —$CONR^8R^9$ (wherein, $R^8$ and $R^9$ each independently represents a hydrogen atom or an alkyl group having 1 to 6 carbon atoms); and
   a compound represented by a general formula (2), the content of the azo compound (1-1) being from 0.02 to 0.5 based on the sum of the content of the azo compound (1-1) and the content of the compound represented by the general formula (2):

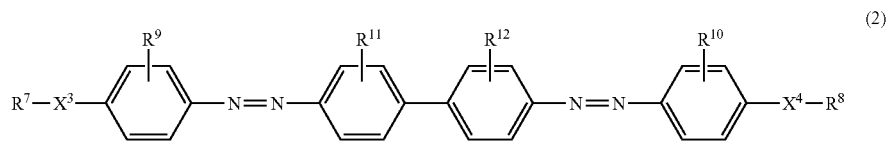

(2)

(wherein, $R^7$ and $R^8$ represent the same groups as those of $R^1$ and $R^2$ in the general formula (1);
   $X^3$ represents the same group as that of $X^1$ in the general formula (1); $X^4$ represents the same group as that of $X^2$ in the general formula (1); $R^9$ and $R^{10}$ each independently represents a carboxy group which may be bonded to an alkali metal to form a salt; and $R^{11}$ and $R^{12}$ represent the same groups as those of $R^5$ and $R^6$ in the general formula (1)).

6. The composition for the photo-alignment film according to claim 5, wherein the azo compound (1-1) is represented by the general formula (1-1') and the general formula (2) is a general formula (2'):

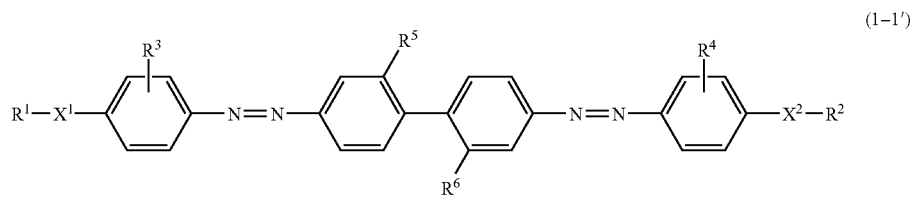

(1-1')

(wherein, $R^1$ to $R^6$, and $X^1$ and $X^2$ represent the same groups as those represented by the general formula (1), and at least one of $R^3$ and $R^4$ represents —$CONR^8R^9$ (wherein $R^8$ and $R^9$ each independently represents a hydrogen atom or an alkyl group having 1 to 6 carbon atoms)):

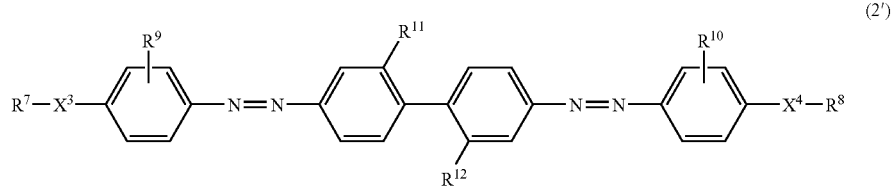

(2')

(wherein, $R^7$ to $R^{12}$, and $X^3$ and $X^4$ represent the same groups as those represented by the general formula (2)).

7. A method for producing a photo-alignment film, comprising:
coating the composition for photo-alignment film according to claim 4 on a substrate; and
irradiating the coated substrate with light having anisotropy.

8. A method for producing a photo-alignment film, comprising:
coating the composition for photo-alignment film according to claim 5 on a substrate; and
irradiating the coated substrate with light having anisotropy.

9. A method for producing a photo-alignment film, comprising:
coating the composition for photo-alignment film according to claim 6 on a substrate; and
irradiating the coated substrate with light having anisotropy.

10. The azo compound according to claim 1, wherein $R^5$ and $R^6$ represent a sulfo group or a salt thereof in the general formula (1).

* * * * *